United States Patent
McCoy et al.

(10) Patent No.: US 6,860,141 B2
(45) Date of Patent: Mar. 1, 2005

(54) METHOD AND APPARATUS FOR DETECTING LEAKS

(75) Inventors: Fred Grant McCoy, Harrison, OH (US); Jonathan Mark Fazekas, Hebron, KY (US); Ryan R. Borntrager, Cleves, OH (US)

(73) Assignee: Cincinnati Test Systems, Inc., Cleves, OH (US)

( * ) Notice: Subject to any disclaimer, the term of this patent is extended or adjusted under 35 U.S.C. 154(b) by 0 days.

(21) Appl. No.: 10/868,158

(22) Filed: Jun. 15, 2004

(65) Prior Publication Data

US 2004/0226345 A1 Nov. 18, 2004

Related U.S. Application Data

(62) Division of application No. 10/382,565, filed on Mar. 6, 2003.

(51) Int. Cl.[7] .......................... G01M 3/04; G08B 28/00
(52) U.S. Cl. ......................... 73/40.7; 702/51; 340/605
(58) Field of Search ............................. 73/40.7; 702/51; 340/605

(56) References Cited

U.S. PATENT DOCUMENTS

| | | |
|---|---|---|
| 1,933,791 A | 11/1933 | Crouch |
| 3,038,542 A | 5/1962 | Loomis |
| 3,087,327 A * | 4/1963 | Kagi ........................... 73/40.7 |
| 3,413,840 A | 12/1968 | Basile et al. |
| 3,591,944 A * | 7/1971 | Wilcox ........................ 53/408 |
| 3,721,898 A | 3/1973 | Dragoumis et al. |
| 3,786,675 A | 1/1974 | Delatorre et al. |
| 3,925,666 A | 12/1975 | Allan et al. |
| 3,942,331 A | 3/1976 | Newman, Jr. et al. |
| 3,949,596 A | 4/1976 | Hawk |
| 4,272,985 A | 6/1981 | Rapson, Jr. et al. |
| 4,308,746 A | 1/1982 | Covington |
| 4,336,708 A | 6/1982 | Hobgood et al. |
| 4,357,113 A | 11/1982 | Brooks |
| 4,500,865 A | 2/1985 | Tanaka et al. |

(List continued on next page.)

OTHER PUBLICATIONS

2002 Microchip Technology Inc., "Stand–Alone CAN Controller with SPI™ Interface", MCP2510, pp. 1–76, http://www.microchip.com (2002).
2002 Microchip Technology Inc., "High–Speed CAN Transceiver", MCP2551, pp. 1–20, http://www.microchip.com (2002).
Analog Devices, Inc., "5 V Low Power EIA RES–485 Transceiver", ADM485, pp. 1–12, www.analog.com (2002).
Analog Devices, Inc., "Ultraprecision Low Noise, 2.048 V/2.500 V/3.00 V/5.00 V XFET® Voltage References", ADR420/ADR421/ADR423/ADR425, pp. 1–16, www.analog.com (2002).
Analog Devices, Inc., "MicroConverter® Quick Reference Guide", ADUC834, www.analog.com/microconverter.
M J Schofield, "Controller Area Network—How CAN Works", pp. 1–5, http.www.mischofield.com/canworks.htm (1996–2003).
Analog Devices, Inc., "MicroConverter®, Dual 15–/24–Bit ADCs with Embedded 62KB Flash MCU", ADUC834, pp. 1–75, www.analog.com (2002).
Microsens SA, "Microsens Thermal Conductivity Sensor," MTCS–2202, pp. 1–4, www.microsens.ch.
"Technical Data" p. 1 www.edwards.boc.com (2003).

*Primary Examiner*—Michael Cygan
(74) *Attorney, Agent, or Firm*—Bose McKinney & Evans LLP

(57) ABSTRACT

The present invention relates to a sensor apparatus configured to detect the presence of a gas, such as a tracer gas and a leak detection apparatus configured to detect the presence of a tracer gas and indicate the location of a leak. The leak detection apparatus may further be configured to quantify the leak rate at the leak location.

18 Claims, 24 Drawing Sheets

U.S. PATENT DOCUMENTS

| | | | |
|---|---|---|---|
| 4,513,605 | A | 4/1985 | Hawerkamp |
| 4,513,615 | A | 4/1985 | Sato et al. |
| 4,529,974 | A | 7/1985 | Tanaka et al. |
| 4,532,795 | A | 8/1985 | Brayman et al. |
| 4,557,139 | A | 12/1985 | Cantwell et al. |
| 4,675,834 | A | 6/1987 | Furuse |
| 4,740,777 | A | 4/1988 | Slocum et al. |
| 4,744,246 | A | 5/1988 | Busta |
| RE33,075 | E | 10/1989 | Holm et al. |
| 4,888,706 | A | 12/1989 | Rush et al. |
| 4,894,639 | A | 1/1990 | Schmierer |
| 5,078,006 | A | 1/1992 | Maresca, Jr. et al. |
| 5,163,314 | A | 11/1992 | Maresca, Jr. et al. |
| 5,170,657 | A | 12/1992 | Maresca, Jr. et al. |
| 5,189,904 | A | 3/1993 | Maresca, Jr. et al. |
| 5,191,785 | A | 3/1993 | Kidd et al. |
| 5,201,212 | A | 4/1993 | Williams |
| 5,202,667 | A | 4/1993 | Alvin |
| 5,225,812 | A | 7/1993 | Faghri |
| 5,373,729 | A * | 12/1994 | Seigeot ............... 73/49.3 |
| 5,376,927 | A | 12/1994 | Kidd |
| 5,394,345 | A | 2/1995 | Berard et al. |
| 5,526,678 | A | 6/1996 | Shaw et al. |
| 5,533,383 | A | 7/1996 | Greene et al. |
| 5,586,050 | A | 12/1996 | Makel et al. |
| 5,594,162 | A | 1/1997 | Dolan et al. |
| 5,610,324 | A | 3/1997 | Lawson |
| 5,656,813 | A | 8/1997 | Moore et al. |
| 5,675,506 | A | 10/1997 | Savic |
| 5,764,150 | A | 6/1998 | Fleury et al. |
| 5,979,227 | A | 11/1999 | Lawson et al. |
| 6,035,701 | A | 3/2000 | Lowry et al. |
| 6,041,645 | A | 3/2000 | Lawson et al. |
| 6,157,033 | A | 12/2000 | Chudnovsky |
| 6,167,750 | B1 * | 1/2001 | Lehmann ............... 73/49.3 |
| 6,182,497 | B1 | 2/2001 | Krajci |
| 6,225,909 | B1 | 5/2001 | Nill, Jr. |
| 6,227,036 | B1 | 5/2001 | Yonak et al. |
| 6,326,894 | B1 | 12/2001 | McGrath |
| 6,345,527 | B1 | 2/2002 | Lehmann |
| 2001/0001149 | A1 | 5/2001 | Alouani et al. |
| 2001/0013832 | A1 | 8/2001 | Chavand |
| 2002/0109577 | A1 | 8/2002 | Loose et al. |
| 2002/0152037 | A1 | 10/2002 | Sunshine et al. |
| 2003/0062175 | A1 | 4/2003 | Olander et al. |
| 2003/0204337 | A1 | 10/2003 | Beutelschiess |
| 2003/0216869 | A1 | 11/2003 | Sunshine |
| 2003/0216949 | A1 | 11/2003 | Kram et al. |

* cited by examiner

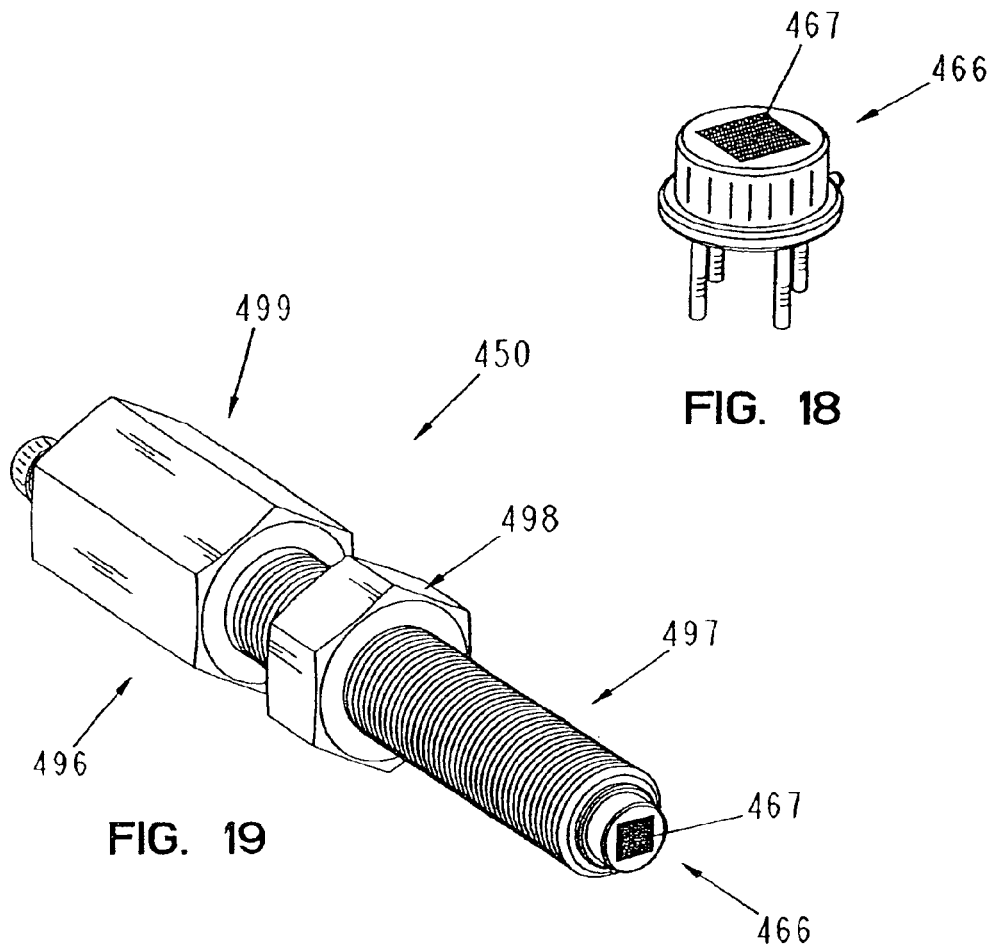
FIG. 18
FIG. 19
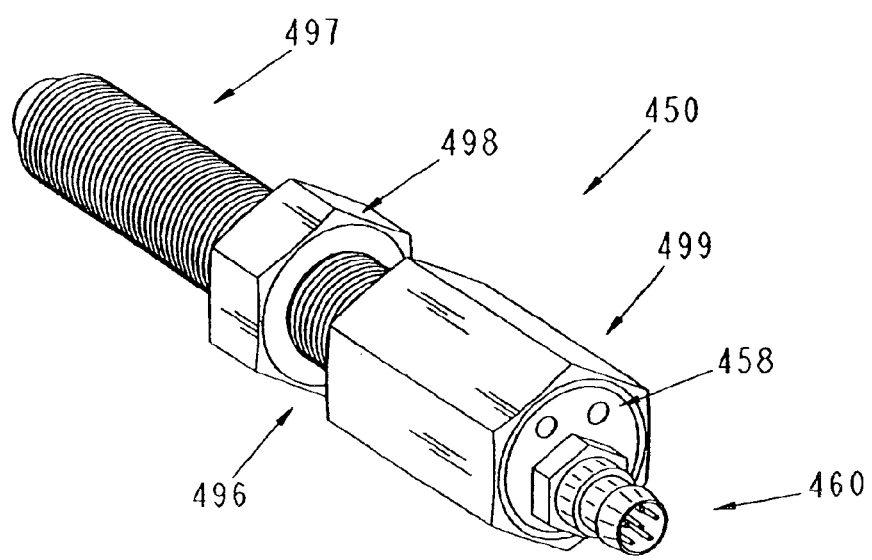
FIG. 20

METHOD AND APPARATUS FOR DETECTING LEAKS

This application is a divisional application of U.S. patent application Ser. No. 10/382,565, filed Mar. 6, 2003, titled "A METHOD AND APPARATUS FOR DETECTING LEAKS", the disclosure of which is expressly incorporated by reference herein.

BACKGROUND AND SUMMARY OF THE INVENTION

The present invention relates to methods and apparatus to detect the presence of a gas and in particular to methods and apparatus for the detection of the presence of a tracer gas in a leak testing environment.

In traditional leak testing apparatus either an interior region or an exterior region of a part under test is placed at a higher pressure than the other of the interior region or exterior region of the part under test. As such, if a leak is present in the part under test, the gas will flow from the higher-pressure side of the part under test to the lower pressure side of the part under test. One method to monitor this flow of gas and hence detect the presence of a leak is with a pressure decay apparatus which monitors the pressure of the higher-pressure side of the part under test. A decrease in pressure could be an indication of a leak. Another method uses a mass spectrometry based apparatus to test for the presence of a tracer gas on the lower pressure side of the part under test. The tracer gas having been introduced on the higher-pressure side of the part under test.

Such apparatus provide the operator of the apparatus with an indication of whether a part under test has a leak or at least whether the part under test has a leak that exceeds a predetermined threshold value. Typically, the customer specifies the threshold value and the operator sets the threshold value of the apparatus. If the operator of the leak testing apparatus receives an indication from the leak testing apparatus that the part under test contains an unacceptable leak, i.e. the leak exceeds the threshold value, the operator knows that the part under test is rejected and the operator places the part in a queue for further testing. However, the operator has no knowledge of the location of the leak or whether subsequently rejected parts are leaking from approximately the same location or a different location.

In order to determine the location of the leak further testing is traditionally required. Once the location of the leak is determined changes can be implemented to the manufacturing process to minimize the number of future rejected parts. The location of the leak is typically determined in one of two methods. First, for larger leaks the location of the leak is determined by pressurizing the rejected part and submerging the rejected part into a water bath. The location of the leak is determined based on the presence of air bubbles emanating from the leak site. Second, for smaller leaks the location of the leak can be determined by pressurizing the rejected part with a tracer gas and passing a tracer gas detector, such as a sniffer apparatus, over the potential leak areas of the rejected part. The tracer gas detector draws the gas proximate to a probe on the tracer gas detector apparatus, into the probe, and past a detector to detect the presence of tracer gas. One method of drawing the gas proximate to the probe is with a fan unit that draws gas into the probe and eventually past the detector. The leak site is then noted and potentially changes to the manufacturing process will be implemented.

The two stage process described above requires additional resources, delays the determination of the location of the leak for a given part under test and delays the determination of whether the location of the leak is repeatable from rejected part to rejected part. Further, the above two stage process is very operator dependent, in that the operator must visually recognize the leak, denote the leak location, and subject each rejected part to a consistent testing procedure. Additionally, results vary from operator to operator in the ability of each operator to recognize leaks and denote leak locations.

In addition, traditional apparatus often use mass spectrometry equipment to detect the presence of a leak due to the need to detect small quantities of the tracer gas. Such apparatus require that the gas located on the lower pressure side of the part under test be drawn to a sensing element to analyze the gas to detect the presence of the tracer gas.

As such, a need exists for a leak detection apparatus that provides an indication of the location of a leak in a part under test generally concurrently with the initial leak testing of the part. Additionally, a need exists for a leak detection apparatus that provides an indication of the location of a leak and an indication or measurement of the leak rate. Further, a need exists for a cost effective leak detection apparatus.

In one exemplary embodiment, the present invention includes a leak testing apparatus configured to detect the presence of a leak in a part under test. The leak testing apparatus of the present invention in one example is further configured to determine the location of the leak in the part under test. In another example the leak testing apparatus is further configured to determine both the location of the leak in the part under test and the leak rate of the corresponding leak.

In another exemplary embodiment, an apparatus for detecting the presence of at least one leak in a first region of a part under test and for localizing the location of the at least one leak, wherein a first side of the first region contains a tracer gas and is at a higher pressure than a second side of the first region such that the tracer gas will emanate through the at least one leak from the first side to the second side comprises a plurality of sensors positioned proximate to the first region, each sensor being configured to detect the presence of a tracer gas emanating from a leak and to provide a sensing signal; and a controller connected to the plurality of sensors. The controller configured to provide a leak detection signal in response to at least a first sensor of the plurality of sensors detecting the presence of the tracer gas, the leak detection signal including leak detection information representative of the location of the leak in the first region based on the sensing signals received from at least the first sensor and a second sensor of the plurality of sensors. In one example, the apparatus further comprises an indicator configured to provide a visual indication of the location of the leak. In one variation, the indicator includes a display configured to display a first representation of the part under test and a sensor icon positioned on the first representation, the sensor icon corresponding to a location of a first sensor which is proximate to the location of the leak. In another variation, the indicator includes a display configured to display a first representation of the part under test and a leak graphic positioned on the first representation, the position of the leak graphic corresponding to a location of a first sensor which is proximate to the location of the leak.

In one exemplary method, a method of monitoring a part under test to determine whether a first region contains a leak, the method comprises the steps of locating a plurality of sensors proximate to the first region, each of the plurality of sensors configured to detect the presence of a tracer gas emanating from the leak and to provide a sensing signal; monitoring each of the plurality of sensors to determine if the tracer gas is being detected by any of the plurality of sensors; and providing a leak detection signal in response to at least a first sensor of the plurality of sensors detecting the presence of the tracer gas, the leak detection signal including leak location information representative of the location of the leak in the first region based on the sensing signals received from at least the first sensor and a second sensor of the plurality of sensors. In one example, the method further comprises the step of providing a first indication of the location of the leak. In one variation, the first indication includes displaying on a display a first representation of a part under test and a sensor icon positioned on the first representation, the sensor icon corresponding to a location of a first sensor which is proximate to the location of the leak. In another variation, the first indication includes displaying on a display a first representation of a part under test and a leak graphic positioned on the first representation, the position of the leak graphic corresponding to a location of a first sensor which is proximate to the location of the leak.

In yet another exemplary embodiment a computer readable media for use in a leak testing application to determine which of a plurality of sensors is proximate to a leak in a part under test comprises a software portion configured to load a data file corresponding to the location of the plurality of sensors, to monitor the plurality of sensors to determine if any of the plurality of sensors has detected the presence of a leak, to determine the location of the leak if at least a first sensor of the plurality of the sensors detected the presence of the leak, and to provide a visual indication of the location of the leak if at least the first sensor of the plurality of the sensors detected the presence of the leak. In one example, the software portion is further configured to provide a first representation of the part under test and a first sensor representation of the at least first sensor positioned on at least the first representation of the part under test. In another example, the visual representation of the at least first sensor is a sensor icon. In yet another example, the software portion is further configured to determine the location of the leak by determining which sensor of the plurality of sensors detected the maximum concentration of a tracer gas emanating from the part under test. In still a further example, the software portion is further configured to determine the location of the leak by determining which sensor of the plurality of sensors first detected the presence of a tracer gas emanating from the part under test. In still yet a further example, the software portion is further configured to determine the leak rate of the leak in the part under test. In one variation, the software portion further configured to provide a leak graphic positioned on the first representation of the part under test at a location proximate to the location of the leak.

In a further exemplary embodiment, the present invention includes a sensor apparatus configured to detect the presence of a gas, such as helium or hydrogen. In one example the sensor apparatus includes a sensor controller and is a networkable sensor apparatus, such that the sensor apparatus is capable of sharing information with other devices across a network. In another example, the sensor apparatus is configured to detect the presence and concentration of a gas, such as helium or hydrogen. In yet another example, the sensor apparatus is configured to be incorporated into a component to detect the presence of a gas.

In yet a further exemplary embodiment, a sensor apparatus for detecting the presence of a leak in a part under test, the part under test being pressurized with a gas including a tracer gas comprises a housing; a sensor configured to detect the presence of the tracer gas and to generate a sensing signal; at least a first portion of the sensor being contained in the housing; and an I/O interface coupled to the housing, the I/O interface being configured to provide a first connection corresponding to an analog output and a second connection corresponding to a network output; and a sensor controller connected to the sensor and the I/O interface and configured to generate an output signal based on the sensing signal generated by the sensor, the sensor controller further configured to determine if a network is present across the second connection of the I/O interface and to generate a data packet for transmission over the network if the network is present, the sensor controller being contained in the housing. In one example, the sensor includes a thermal conductivity transducer. In one variation, a portion of the thermal conductivity transducer is accessible from an exterior of the housing and is positioned proximate to the exterior of the housing. In another example, the sensor controller is configured to detect the presence of a first network and the presence of at least one additional network. In one variation, the sensor controller is configured to provide the analog output over the first connection when neither the first network nor the at least one additional network are present. In yet another example, the sensor apparatus is a stand-alone leak detection apparatus, the sensor apparatus further comprising a power supply positioned within the housing and coupled to at least the sensor controller and an indicator viewable from the exterior of the housing, the indicator being configured to provide an indication of the presence of the tracer gas.

In still a further exemplary embodiment, a gas sensor apparatus for detecting the presence of a gas comprises a housing including a first outer surface; a sensor configured to detect the presence of the gas and to generate a sensing signal, the sensor including a transducer portion, the transducer portion positioned proximate to the first outer surface of the housing such that the transducer portion is contactable by the gas; a sensor controller connected to the sensor and configured to generate an output signal based on the sensing signal generated by the sensor; and wherein at least a portion of the sensor and the sensor controller are contained within the housing. In one example, the gas sensor apparatus further comprises an I/O interface being coupled to the housing and configured to connect the sensor controller to at least one device remote from the gas sensor apparatus. In one variation, the output signal of the sensor controller is a scaled analog output signal representative of the amount of the gas detected by the sensor, the scaled analog output signal being made available to the at least one remote device through a first connection of the I/O interface. In another variation, the output signal of the sensor controller is a digital signal representative of the amount of the gas detected by the sensor, the digital signal being made available to the at least one remote device through a second connection of the I/O interface. In still another variation, the I/O interface further includes at least one transceiver configured to receive the digital signal from the sensor controller and to generate and transmit a data packet containing the digital signal. In another example, the gas sensor further comprises an indicator configured to provide a visible indication signal, the visible indication signal being representative of the presence of the gas and the visible indication signal being viewable from the exterior of the housing.

In still another exemplary embodiment, a sensor apparatus for use with a network comprises a housing; a sensor configured to detect the presence of a tracer gas and to generate a sensing signal, the sensor including a first sensing portion, the first sensing portion being positioned such that the first sensing portion is contactable by the tracer gas; a sensor controller connected to the sensor and configured to generate an output signal based on the sensing signal generated by the sensor; a network controller connected to the sensor controller and configured to generate a network data packet, the network data packet including information based on the output signal generated by the sensor controller; a network interface connected to the network controller and adapted to connect the sensor apparatus to the network; wherein the housing is configured to contain at least a first portion of the sensor, the sensor controller and the network controller. In one example, the sensor includes a thermal conductivity transducer. In still another example, the sensor apparatus further comprises an indicator coupled to the sensor controller, the indicator including a first indicator configured to provide status information related to the sensor apparatus and a second indicator configured to provide an indication of the presence of the tracer gas.

Additional features of the present invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description of exemplary embodiments particularly refers to the accompanying figures in which:

FIG. 18 is a perspective view of a thermal conductivity sensory element for use in a sensor apparatus, such as the sensor apparatus of FIGS. 14–17;

FIG. 19 is a first perspective view of an exterior of the sensor apparatus of FIG. 17 incorporating the thermal conductivity sensor of FIG. 18;

FIG. 20 is a second perspective view of the exterior of the sensor apparatus of FIG. 17 showing an indicator and an I/O interface;

DETAILED DESCRIPTION

Figure 1:
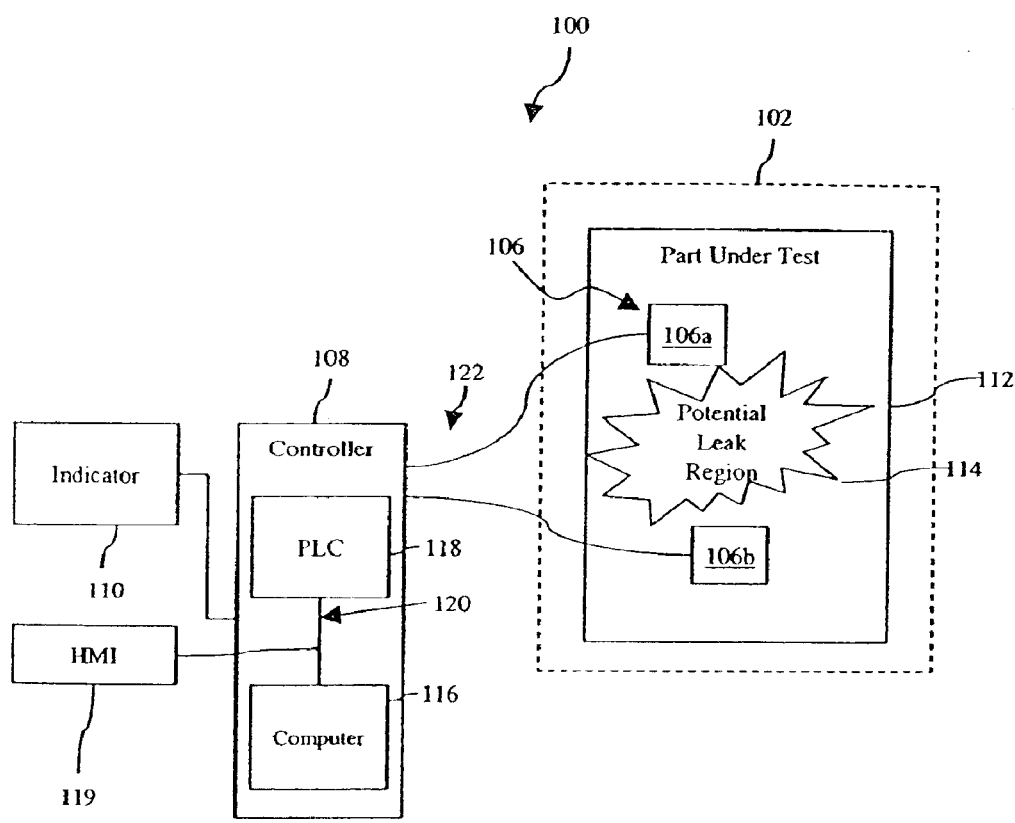
FIG. 1 is a diagrammatic representation of a leak testing apparatus of the present invention configured to test for a leak in a part under test having a first potential leak region.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

A Leak Detection Apparatus

Referring to FIG. 1, a diagrammatic representation of a leak testing apparatus 100 according to the present invention is shown. Leak testing apparatus 100 includes a test region 102, a plurality of sensors 106 (of which sensors 106a and 106b are shown for illustration), a controller 108, and an indicator 110. Although only two sensors, 106a and 106b are shown in FIG. 1, it is contemplated that plurality of sensors 106 includes two, three or more sensors. Test region 102 is configured to receive a part under test 112 having at least a first potential leak region 114. Example potential leak regions include weld regions and joints. However, in one example the entire surface of a part under test or a portion thereof may be tested for potential leaks and therefore the entire surface or portion thereof may be considered a potential leak region. In one example, test region 102 includes at least one fixture (not shown) configured to hold part under test 112 and configured to position the plurality of sensors 106 relative to potential leak region 114 of part under test 112. In another embodiment, test region 102 further includes a pressure chamber (not shown). The pressure chamber being configured to pressurize a volume of air around part under test 112.

In the illustrated embodiment, controller 108 includes a computer 116 and a programmable logic controller (PLC) 118. Computer 116 is configured to process data received from the plurality of sensors 106, identify the location of a leak, provide a signal to indicator 110 of the location of the leak, and to provide for the ability of the leak data to be stored for future analysis. In another embodiment, computer 116 is further configured to quantify the leak rate of the leak and to provide a signal to indicator 110 of the leak rate. An exemplary computer 116 is an EMAC Industrial computer available from EMAC, Inc. located at P.O. Box 2042, Carbondale, Ill. 62902.

PLC 118 is configured to control the physical motions of leak testing apparatus 100. An exemplary PLC 118 is a Model No. SLC 5/05 available from Allen Bradley through Rockwell Automation located at US Bank Center, 777 East Wisconsin Avenue, Suite 1400 Milwaukee, Wis. 53202. In one example, PLC 118 is configured to actuate components, such as cylinders, to secure part under test 112 in the corresponding fixture or fixtures of test region 102 configured to secure part under test 112 and to position plurality of sensors 106a and 106b proximate to potential leak region 114. PLC 118 is further configured to control the filling and evacuating of the part under test 112 with a tracer gas. In an alternative embodiment PLC 118 is configured to control the filing and evacuating of the pressure chamber of test region 102 with a tracer gas. The use of a PLC to control the filing and evacuating of the part under test with a tracer gas, such as PLC 118, is well known in the art.

PLC 118 is further connected to a human-machine interface (HMI) 119. HMI 119 provides an exemplary interface for the operator of leak testing apparatus 100 to input parameter values to leak testing apparatus 100, such as a setpoint or leak rate which corresponds to an unacceptable leak in the part under test and/or a test timer value to control the length of a test cycle for part under test 112. An exemplary HMI is a Panelview standard terminal from Allen Bradley through Rockwell Automation located at US Bank Center, 777 East Wisconsin Avenue, Suite 1400 Milwaukee, Wis. 53202. In the illustrated embodiment HMI 119 is linked to controller 108 through a network, such as network 120 discussed below. In an alternative embodiment, HMI 119 is directly connected to controller 108.

In another embodiment PLC 118 is provided parameter values across a network, such as network 120, from from computer 116 or from a remote computer (not shown). In a further embodiment PLC 118 is provided parameter values from a computer readable media (not shown) removably coupled to PLC 118 or computer 116 or a remote computer (not shown).

In one embodiment of leak testing apparatus 100, PLC 118 is further configured to perform an initial knock-out or gross leak test on part under test 112, such as a pressure decay test. It is well known in the art to use a PLC, such as PLC 118, to perform a pressure decay test on a part under test. If part 112 fails the gross leak test then the part under test 112 does not need to be tested with the more accurate tracer gas or fine leak test described below unless it is desired to pin-point the location of the gross leak. In one variation, the gross leak test, such as the pressure decay test is conducted simultaneously with the fine leak test. When a pressure decay test and the fine leak test are conducted simultaneously, the pressure decay test uses a gas containing the tracer gas.

In the illustrated embodiment, computer 116 and PLC 118 are linked together through network 120. Network 120 is configured to permit computer 116 and PLC 118 to share information. Exemplary networks include wired networks, wireless networks, such as an RF network, an IR network, or a cellular network, local area networks, such as an Ethernet network or a token ring network, wide area networks, a controller area network (CAN), connections to the Internet or an Intranet, a RS232 connection, an RS485 connection, or other suitable networks or methods of connecting computer 116 and PLC 118. Computer 116 and PLC 118 can be connected to additional devices across network 120, such as remote computers (not shown) in quality control or to control devices positioned at various stations in the manufacturing process of part under test 112. As such, feedback can be instantly provided to quality control personnel or manufacturing personnel concerning the location of leaks in rejected parts and of any correlation between the leak locations of the rejected parts.

In an alternative embodiment, controller 108 is comprised of a single computer, such as computer 116 which is configured to perform the above-described functions of both computer 116 and PLC 118. In one example, HMI 119 is a touch screen, a light pen, a mouse, a roller ball, or a keyboard.

As stated earlier, for a fine leak test, controller 108 is configured to provide a gas including a tracer gas to either an interior of part under test 112 or an exterior of part under test 112. It is well known in the art to seal a part under test so that the tracer gas is retained on either the interior or exterior of part under test 112 in the absence of a leak in part under test 112. If the tracer gas is provided to the interior of the part under test then test region 102 does not require a pressure chamber while if the tracer gas is provided to the exterior of the part under test 112 then the test region 102 includes a pressure chamber (not shown) to permit the exterior of the part under test 112 to be pressurized.

The tracer gas is introduced to either the interior or the exterior of part under test 112 such that the interior or exterior including the tracer gas is at a higher pressure relative to the other of the interior or exterior not including the tracer gas. Therefore, a pressure difference is created between the interior of part under test 112 and the exterior of part under test 112, the higher pressure region corresponding to the region containing the tracer gas. As such, if part under test 112 includes a leak, the tracer gas will emanate or flow from the higher pressure region to the lower pressure region. In one example the tracer gas is helium. In another example the tracer gas is hydrogen.

Leak testing apparatus 100 is configured to detect the presence of a leak in part under test 112, as indicated by the presence of the tracer gas in the lower pressure region. Leak testing apparatus 100 is further configured to run a leak test whereby part under test 112 is monitored for leaks for a time period corresponding to a value of the test timer provided to PLC 118. As shown in FIG. 1, sensors 106 are placed proximate to potential leak region 114. As stated before it is contemplated to position more than two sensors 106 proximate to region 114. Sensors 106 are connected to controller 108 and are configured to provide a sensing signal, representative of the detection of the tracer gas. In one example the sensing signal is proportional to the concentration of the tracer gas. In the illustrated embodiment, sensors 106a and 106b are connected to controller 108 over a network 122, network 122 being generally similar to network 120, such that sensors 106a and 106b each generate a sensing signal and provide the sensing signal to controller 108 across network 122 as a network message or data packet. In one example network 122 and network 120 are portions of the same network. In an alternative embodiment, the sensors 106 are connected to controller 108 directly such that controller 108 receives a sensing signal from each sensor as a direct input, such as an analog signal.

Controller 108 is configured to receive the sensing signals from sensors 106 and to determine if the sensing signals indicate that a leak is present in part under test 112. As explained in more detail below, the location of the leak can be deduced by monitoring the individual sensing signals from sensors 106. Further, as explained in detail below, if the sensors define an area of containment or accumulation volume the leak rate of leak can be deduced or quantified by monitoring the aggregate sensing signals, such as the sensing signals from both sensors 106.

Indicator 110 is connected to controller 108 and configured to provide an indication signal to an operator of leak testing apparatus 100 of the presence and location of a leak in part under test 112. Controller 108 is configured to provide a leak detection signal to indicator 110 in response to at least one of sensors 106a and 106b detecting the presence of the tracer gas. Further, the leak detection signal of controller 108 can be provided to other devices such as a remote controller (not shown). The leak detection signal including information representative of the location of the leak and/or information related to the leak rate of the leak.

In the illustrated embodiment indicator 110 is directly connected to controller 108. In another embodiment, indicator 110 is linked to controller 108 over a network, such as network 120. Example indication signals include a signal to a network device containing the location of the leak, an audio message, a visual text message of the location of the leak, or a visual image of the part under test with a leak graphic placed at the location of the leak. In one embodiment, indicator 110 is further configured to provide an indication of the leak rate of the leak. The indication of the leak rate can be included in the same signal as the location of the leak or sent in a second indication signal.

Figure 2:
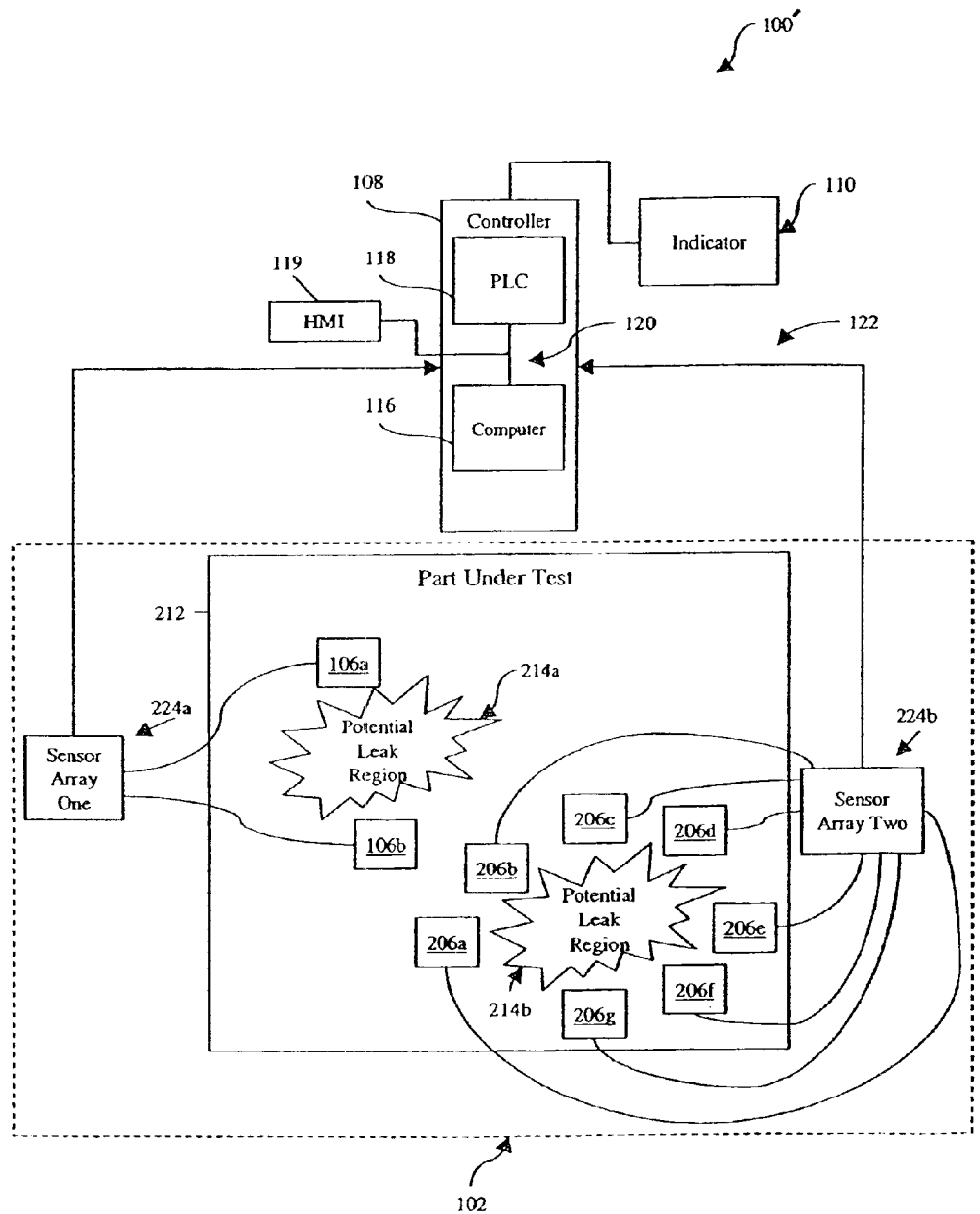
FIG. 2 is a diagrammatic representation of the leak testing apparatus of FIG. 1 configured to test for a leak in a part under test having at least a first and a second potential leak regions.

Referring to FIG. 2, a leak testing apparatus 100' is shown in a configuration for monitoring a part under test 212 having at least two potential leak regions 214a and 214b. Leak testing apparatus 100' is generally similar to leak testing apparatus 100. As such, like numerals are used for components that are common to both leak testing apparatus 100 and leak testing apparatus 100'. As shown in FIG. 2, a first sensor array 224a comprising a plurality of sensors such as sensors 106a and 106b is positioned proximate to a first potential leak region 214a and a second sensor array 224b comprising a plurality of sensors such as sensors 206a, 206b, 206c, 206d, 206e, 206f, and 206g is positioned proximate a second potential leak region 214b. Sensors 206a–g are generally identical to sensors 106a and 106b. Each sensor array 224a and 224b is connected to controller 108. As stated above the sensors are connected to controller 108 either through a network, such as network 122 or directly.

In one embodiment sensor arrays 224a and 224b simply denote the sensor grouping, sensors 106a and 106b and sensor 206a–g, respectively. In another embodiment sensor arrays 224a and 224b correspond to network devices configured to relay network traffic from the respective sensors to other network components, such as controller 108. In one example, sensor arrays 224a and 224b are network routers. In yet another embodiment, sensor arrays 224a and 224b are controllers and are configured to receive data from the respective sensors and to compile network messages to other network devices based on the data received from the respective sensors. In one example the respective sensors are linked to the sensor array controllers through a network similar to network 122. In another example the respective sensors are directly connected to the sensor array controllers and provide an analog output. The network messages compiled by the sensor array controller may be the relaying of signals from the respective sensors, an indication of a leak location, or an indication of the leak rate of a leak.

Although the present invention may be practiced with a single sensor positioned proximate to region 214a and a single sensor positioned proximate to region 214b, the more sensors that are positioned proximate to either potential leak region 214a or 214b the greater the accuracy of leak detection apparatus 100' in determining the location of the leak and/or the quantification of the leak rate. As such, it is preferred to connect sensors 206a–g, 106a and 106b to controller 108 through a network because such a connection allows for many sensors to communicate with controller 108 without requiring that controller 108 to have a multitude of data inputs, only access to a network.

Figure 3:
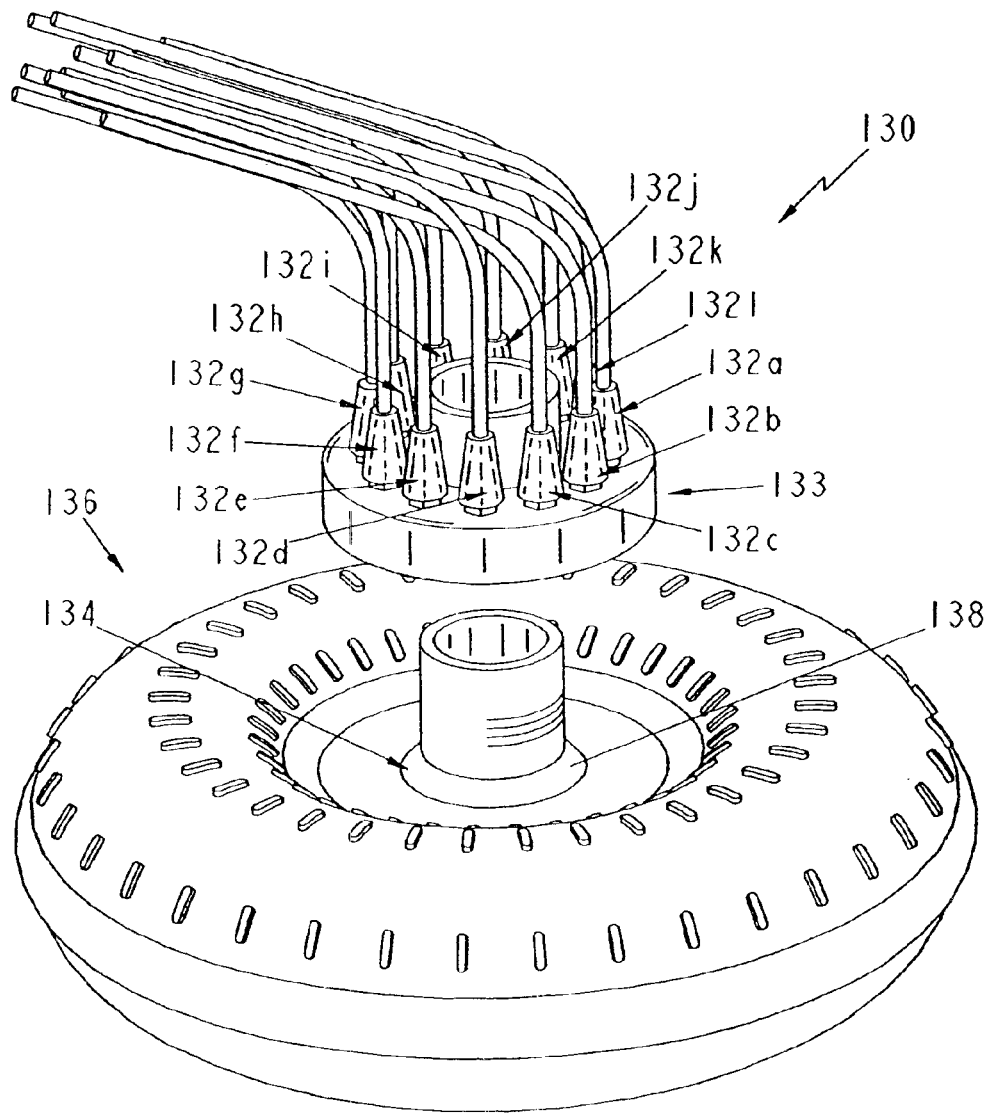
FIG. 3 is a perspective view of a sensor array comprising a plurality of sensors and a fixture whereto the plurality of sensors are affixed, the plurality of sensors being positioned adjacent a part under test having a first potential leak region, the part under test being a torque converter and the first potential leak region being a weld joint.
Figure 4A:
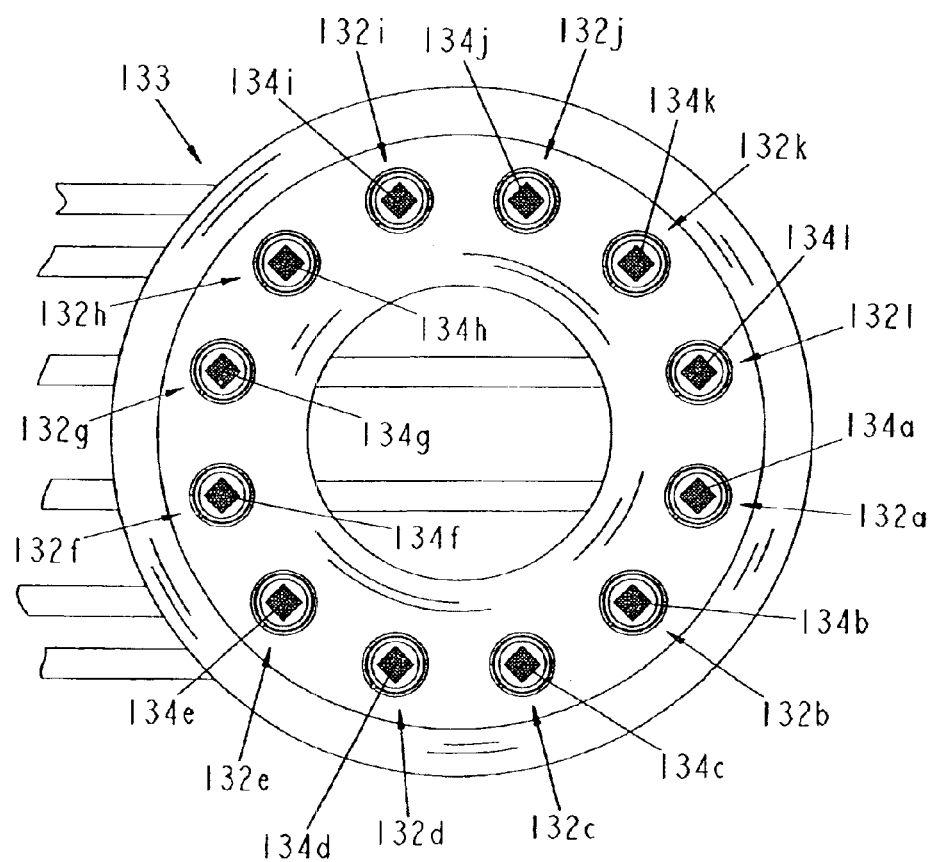
FIG. 4A is a bottom view of the sensor array and the fixture of FIG. 3 showing a sensing element of each of the plurality of sensors.
Figure 4B:
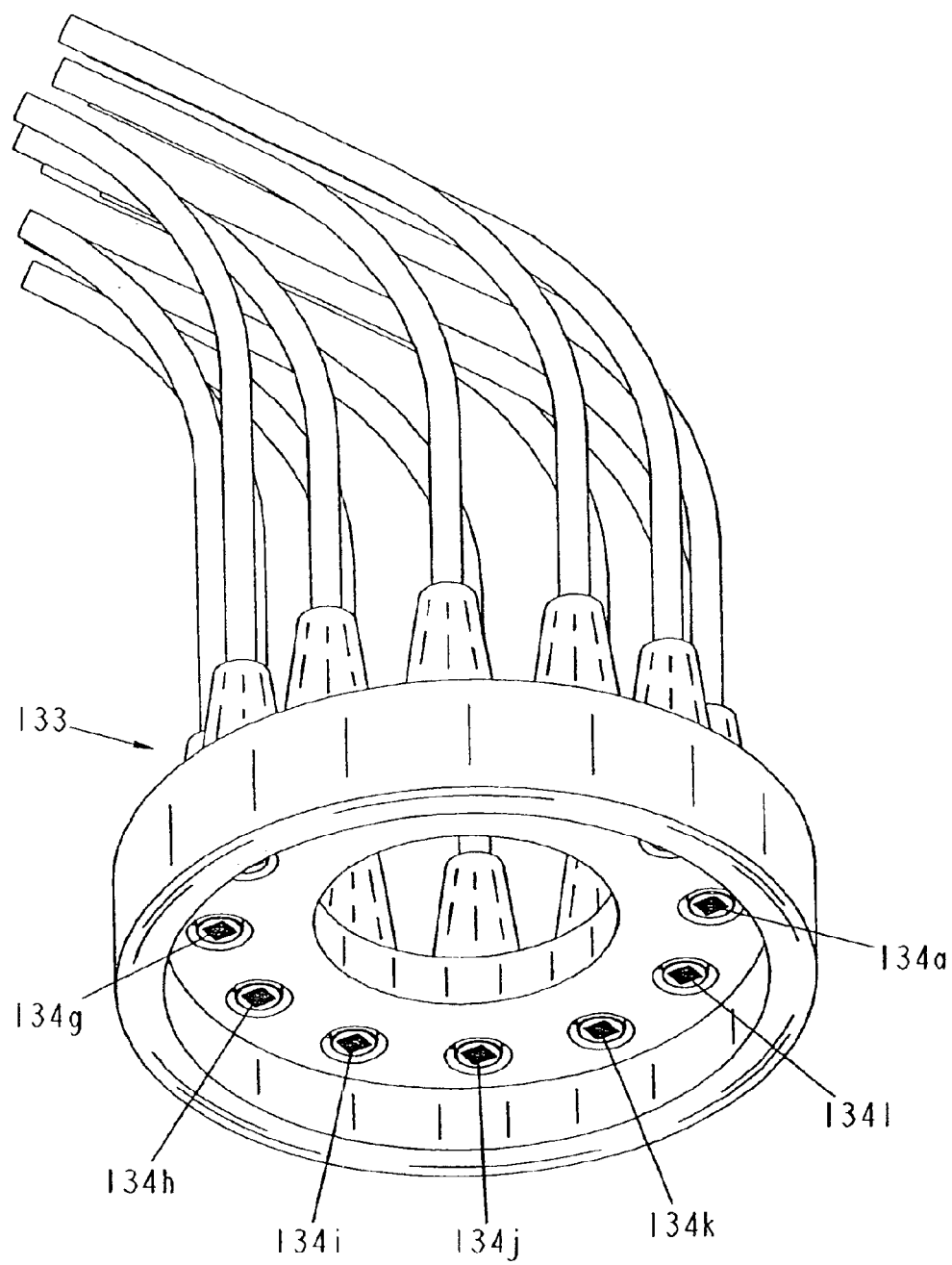
FIG. 4B is a perspective view of the sensor array and the fixture of FIG. 3.

Referring to FIG. 3, an exemplary sensor array 130 includes a plurality of sensors 132a–l. Sensor array 130 is configured to be used with leak testing apparatus 100 or with leak testing apparatus 100'. As shown in FIG. 4a, each sensor 132a–l includes a sensing element or transducer 134a–l. In a preferred embodiment sensors 132a–l are configured to interface with a network, such as a Controller Area Network (CAN) network or an RS485 network. An exemplary sensor for use over either a CAN network or an RS-485 is sensor 300 shown in FIGS. 14–24 below. As explained below, in connection with sensor 300, sensing element or transducer 134a–l of sensor 132a–l is configured to detect the presence of the tracer gas when the tracer gas is in contact with sensing element or transducer 134a–l. Although sensor 300 as described below is capable of functioning in both an analog mode and a network mode, it is to be understood that sensors 132a–l in the preferred embodiment need only to be capable of functioning in the network mode and further only need to be configured for one network, such as either RS-485 or CAN. In alternative embodiments, sensors 132a–l are configured for two or more networks.

Figure 5:
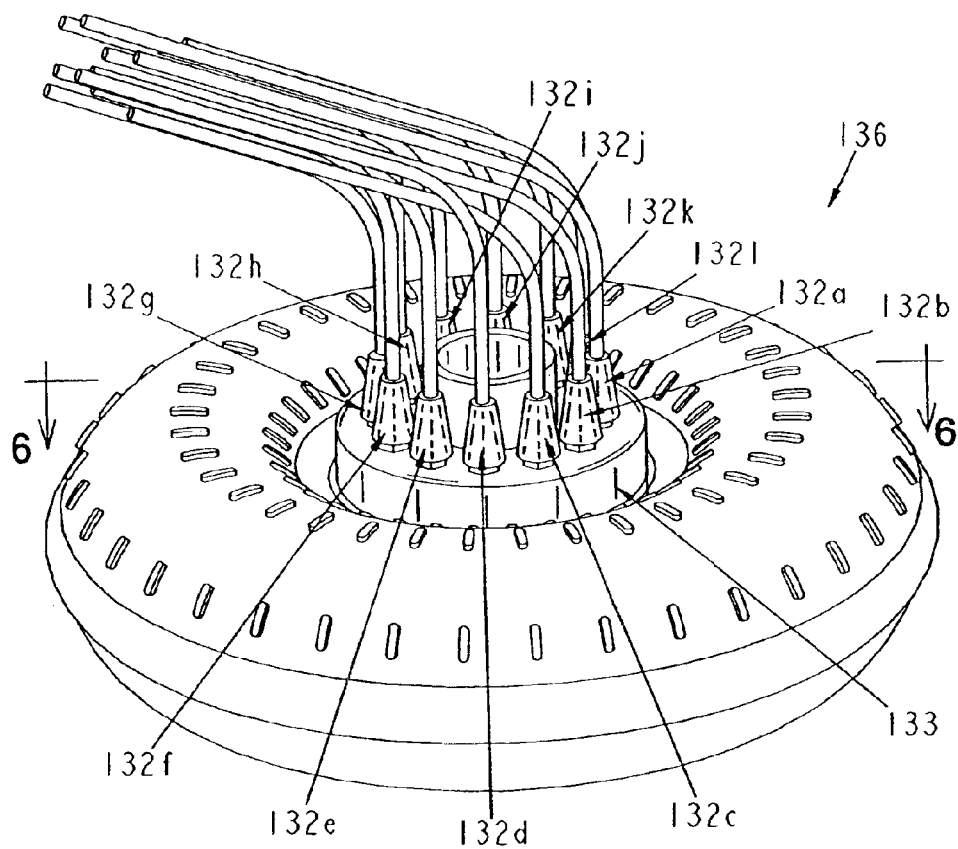
FIG. 5 is a perspective view of the sensor array, the fixture, and part under test of FIG. 3 showing the sensor array and the fixture adjacent the part under test.
Figure 6:
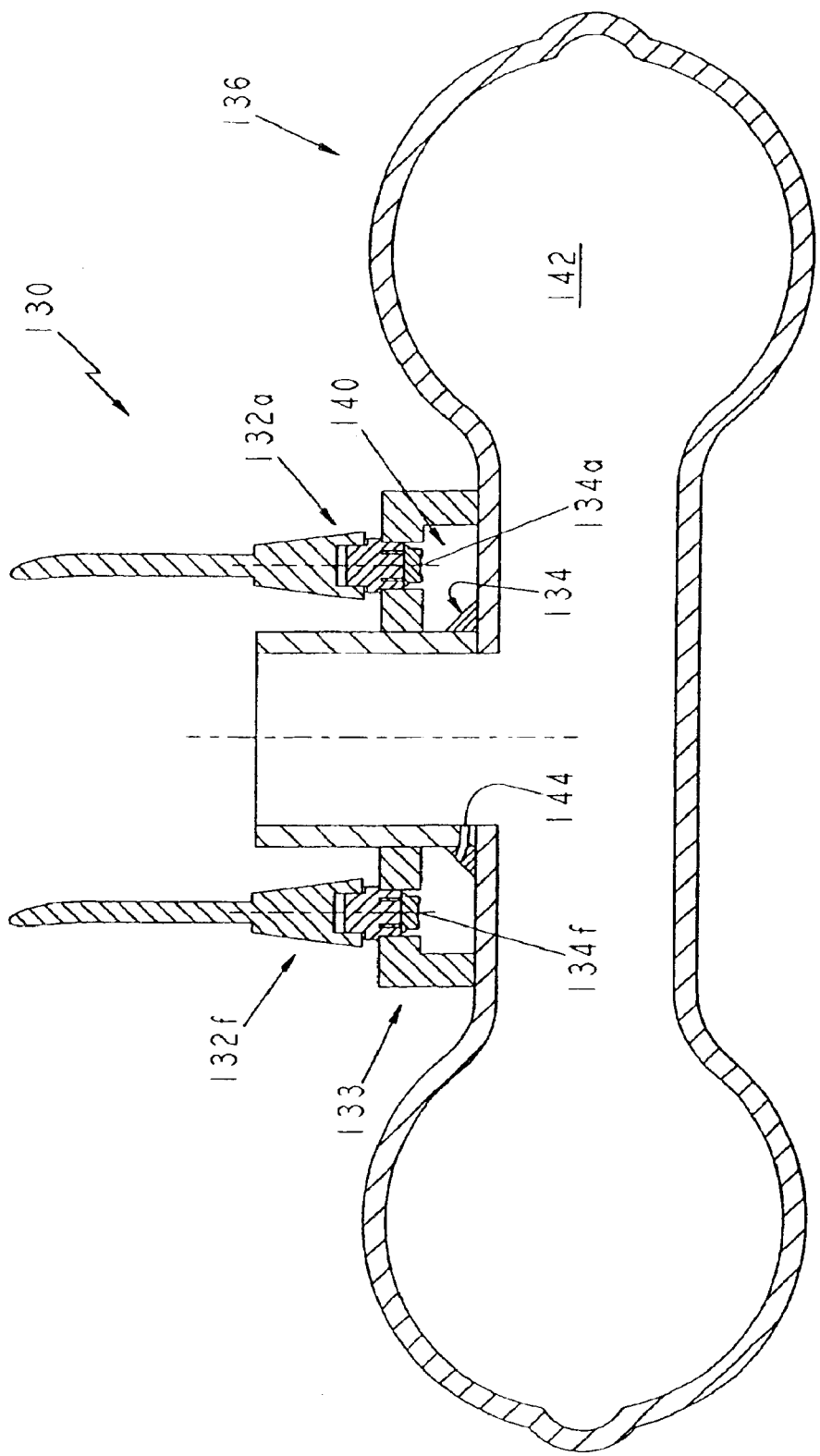
FIG. 6 is a cross section of FIG. 5 along lines 6—6 showing the positioning of a first sensor and a second sensor in the sensor array relative to the position of the first potential leak region.

Sensors 132a–l of sensor array 130 are affixed in a fixture 133 such that sensor array 130 is easy to position relative to a potential leak area of a part under test, such as a weld 134 of torque converter 136 shown in FIGS. 3, 5 and 6. Fixture 133 is configured to position sensors 132a–l proximate to weld 134 of torque converter 136 in a repeatable fashion such that sensor 132a is always placed next to portion 138 of weld 134. As such, if a leak is present in portion 138 of weld 134 in a first torque converter 136 and a subsequent torque converter 136 the same sensor, sensor 132a, will be denoted as being proximate to the leak.

As shown in FIGS. 3, 4a, 4b, 5 and 6, fixture 133 is configured to define in cooperation with part 134 an interior region or accumulation volume 140 (shown in FIG. 6) wherein any emanating tracer gas from an interior region 142 of part 136 through a leak such as leak 144 in weld 134 will be collected. The emanating tracer gas is collected within interior region 140 such that the change in concentration of the tracer gas over time may be monitored to quantify the leak rate of the leak. In one example, interior region 142 is not a sealed region, in order to prevent a pressure buildup in interior region 142 and hence a slowing of leak 144 which could lead to an inaccurate calculation of the corresponding leak rate.

In an alternative embodiment, the fixture for securing the sensor array supports the sensors and positions the sensors repeatably in relation to the potential leak region. However, the fixture does not define an interior region wherein emanating tracer gas collects. As such, the fixture does not permit an accurate estimate of the leak rate only an indication of the location of the leak relative to the potential leak region.

Referring to FIG. 6, sensor 132f is positioned proximate to leak 144. As such, sensing element 134f will detect the presence of the tracer gas emanating from leak 144 before sensing element 134a of sensor 132a will detect the presence of the tracer gas. Further, over time sensor 132f will have a maximum response compared to sensor 132a meaning that sensor 132f will detect a higher concentration of the tracer gas than sensor 132a. As explained below, one or both of these facts is used to determine the location of leak 144. Further, as explained below the summation and average of the response of all sensors 132a–l is used to determine the leak rate associated with leak 144 when the geometry of fixture 133 is such that the tracer gas emanating from leak 144 is generally retained in interior region 140.

Referring to FIGS. 7–10, an exemplary embodiment of a leak testing software 600 is shown. Leak testing software 600 is configured to be executed by controller 108 in association with a fine leak test. For examples for the testing of part 136 of FIGS. 3, 5, and 6, software 600 is configured to associate sensor array 130 and sensors 132a–l relative to test part 136, to monitor signals provided by sensors 132a–l over a network, such as network 122, and to provide an indication of the location of leak 144 and/or to provide an indication of the leak rate associated with leak 144. In one example, controller 108 as a leak detection signal provides the indication of the location of leak 144 and/or the leak rate of leak 144. It is contemplated that software 600 is configured to monitor multiple sensor arrays. In the illustrated embodiment shown in FIGS. 7–10, leak testing software 600 is executed by computer 116 and receives information from and sends information to PLC 118. In an alternative embodiment, leak testing software 600 is partially executed by computer 116 and partially executed by PLC 118. In yet a further alternative embodiment at least a portion of the functionality of software 600 is provided as firmware. In another alternative embodiment, software 600 is executed by a remote computer and commands are provided to controller 108 over a network, such as network 120.

In one embodiment, software 600 is available as one or more files on a portable computer readable media, such as a diskette, a CD-Rom, a Zip disk, a tape, a memory card, or a flash memory card. Software 600 in one example includes an installation program configured to load software 600 on computer 116 and/or to configure software 600. In an alternative embodiment, software 600 and/or an installation program is available across a network as one or more downloadable files.

Figure 7:
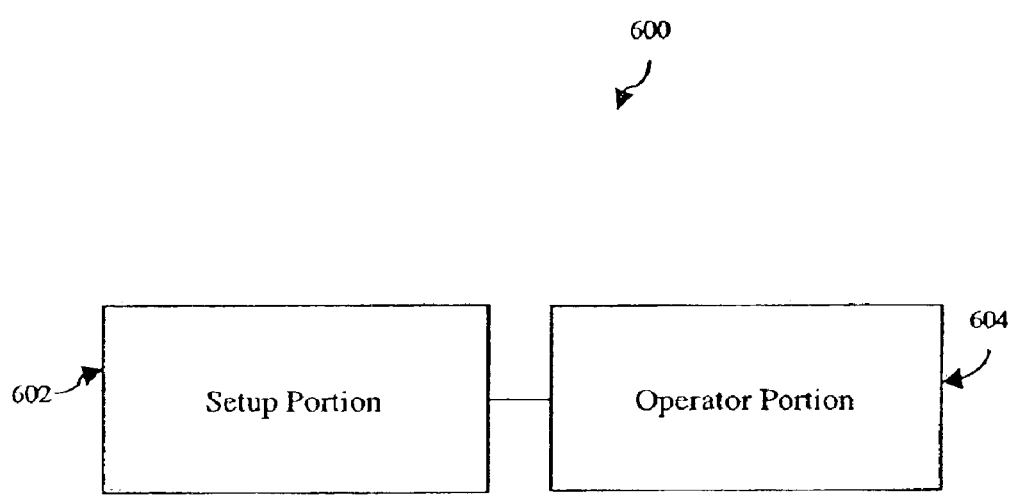
FIG. 7 is a flow chart of a first exemplary embodiment of leak testing software, the leak testing software having a set up portion and a operator portion.

Referring to FIG. 7, leak testing software 600 includes a setup portion 602 configured to allow an operator to set a variety of parameters related to a particular job, such as the testing of a particular part under test, for instance part 136, and a operator portion 604 configured to be used by the operator preparing to leak test a part. Operator portion 604 is configured to load the parameters set for a particular part under test and to execute a testing routine 656 to test a first part for a leak.

Figure 8:
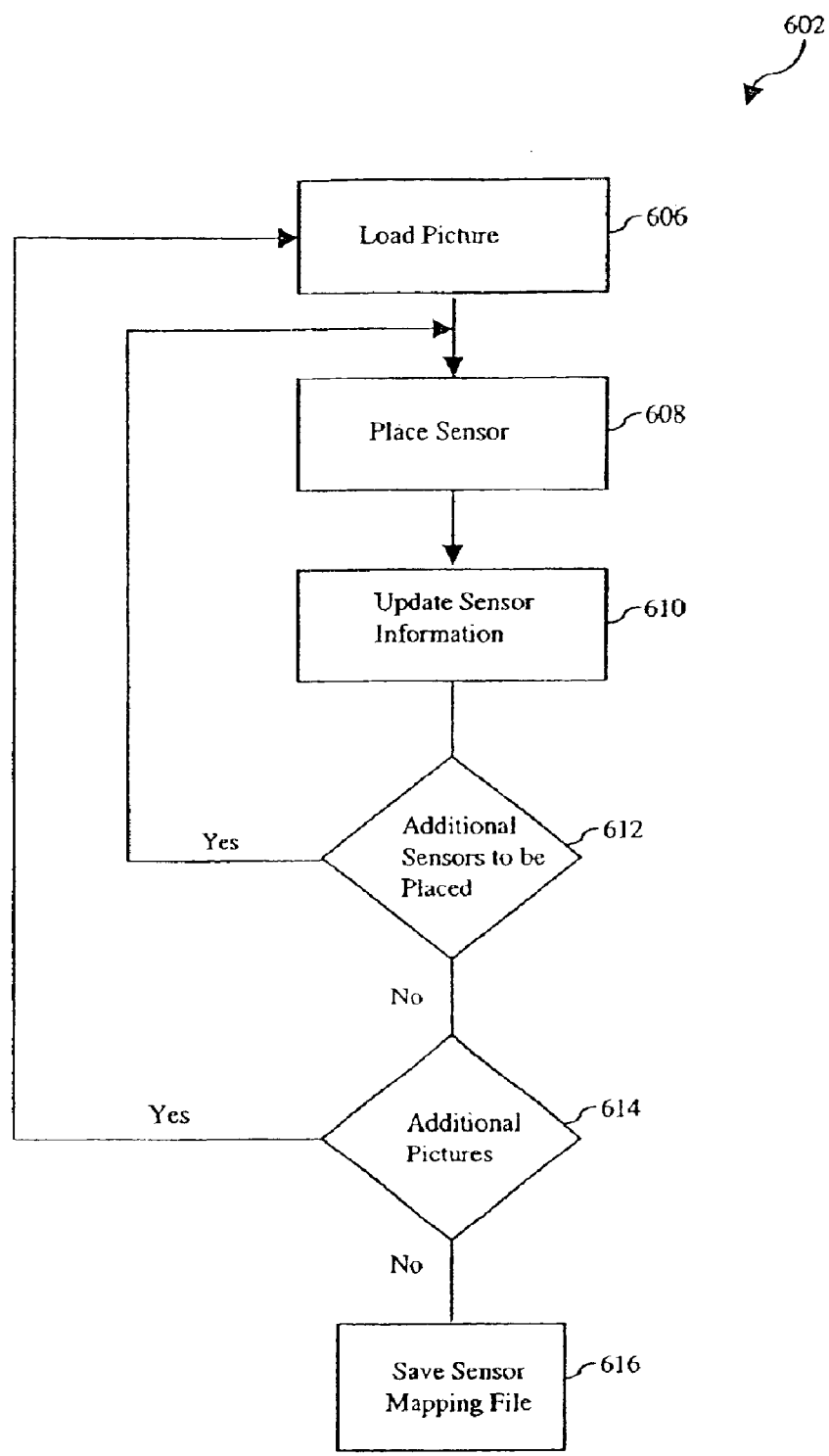
FIG. 8 is a flow chart showing a first exemplary embodiment of the set up portion of the leak testing software of FIG. 7.

Referring to FIG. 8, an exemplary setup portion 602 of software 600 is shown. As represented by block 606, at least a first picture representative of the part to be tested is loaded. The picture is used to provide a visual indication to the operator of the location of the leak. In a first example, the picture corresponds to a still image of a physical part. In a second example, the picture corresponds to a view produced from an electronic database of the part such as a CAD software package. In a third example, the picture corresponds to a three dimensional solid model of the part produced from an electronic database such as a CAD software package.

Figure 13A:
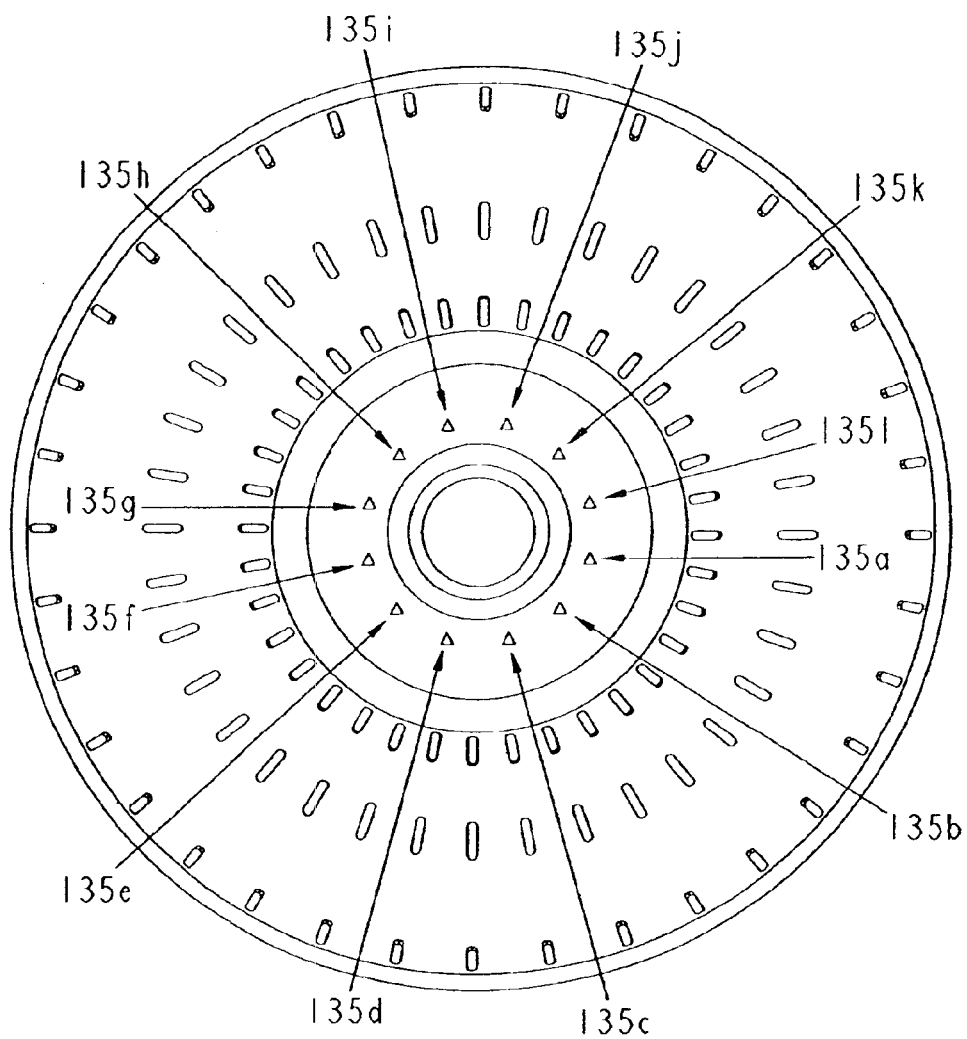
FIG. 13a shows a plurality of example sensor icon overlaid on a picture of a part under test.

As represented by block 608, the operator places a representation of a sensor, such as sensor 132a, on the picture of the part to be tested. In one embodiment the representation of the sensor is a sensor icon, see FIG. 13a for an example sensor icon such as sensor icon 135a. The sensor icon shown in FIG. 13a is a triangular shape. However, it is contemplated that the sensor icon could be a variety of shapes and could include text such that a sensor number and/or sensor name is displayed. The location of sensor 132a on the picture corresponds to the location of the physical sensor 132a relative to part 136 during the testing of part 136. However, updating the location of sensor 132a on the picture does not move the location of sensor 132a on the physical part. The location of sensor 132a on the picture is simply a representation of the location of sensor 132a on the physical part. The operator then updates the information related to sensor 132a, as represented by block 610. Example sensor information to be updated includes a name for sensor 132a, a network id for sensor 132a, sensor position data, which sensor group or array 130 sensor 132a is associated with, and a display priority for sensor 132a or the picture currently displayed. The display priority is a parameter associated with the preferred view to show a leak emanating from sensor 132a. In the case of a picture the display primary parameter indicates the default view to use during operator portion 604.

Software 600 queries whether additional sensors are to be displayed on the current picture of the part to be tested, as represented by block 612. If additional sensor locations are visible in the current picture, the operator selects yes and repeats the above process for the additional sensors. If additional sensors are not visible in the current picture, the operator should select no which leads software 600 to query whether additional pictures of the part to be tested are to be loaded, as represented by block 614. If additional pictures are to be loaded, the operator selects yes and software 600 will loop back to block 606. Otherwise, the operator is prompted to save the sensor mapping file corresponding to the part to be tested, as represented by block 616. The sensor mapping file includes the information entered during the setup portion 602. In one example, the sensor mapping file is a text file which includes at least references to the pictures of the part to be tested, the sensors included on each picture, the sensor positions for each picture and the sensor parameters for each picture.

Figure 9:
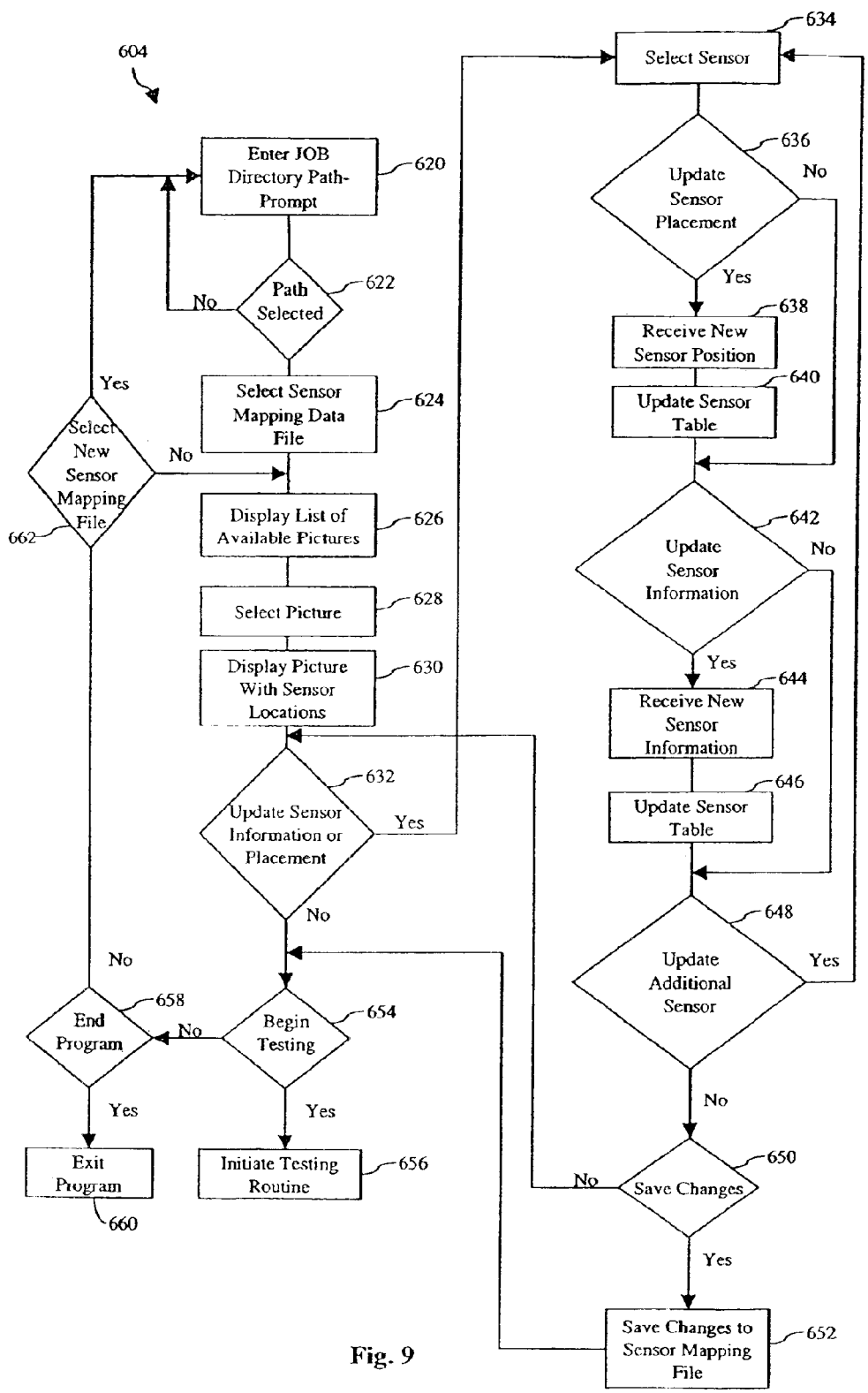
FIG. 9 is a flow chart showing a first exemplary embodiment of the operator portion of the leak detection software of FIG. 7.

Turning to FIG. 9, operator portion 604 of software 600 is shown. As represented by block 620, the operator upon initiating operator portion 604 enters or selects the location of the directory containing the sensor mapping file corresponding to the current part under test, such as part 136. If the operator does not select a proper path the operator is again required to enter or select the directory, as represented by block 622. Otherwise, if a proper path is selected, the operator next selects the correct sensor mapping file 616, as represented by block 624.

The sensor mapping file is loaded into a memory of controller 108 and the operator is presented with a list of pictures of the part under test contained within the sensor mapping file, as represented by block 626. The operator selects a picture from the list and the selected picture along with the sensor icons 135 are displayed on a corresponding display, as represented by blocks 628 and 630. By having the operator select a picture for viewing, a visual check can be done by the operator to insure that the selected sensor mapping file corresponds to the part to be tested.

At this point the operator can make changes to the sensor information or sensor placement or proceed to begin testing, as represented by block 632. If updates are required the operator selects the sensor to be updated, as represented by block 634. The operator can update the placement of a selected sensor by manually inputting new position information or by moving the corresponding sensor icon 135 relative to the picture of the part. However, the user is only changing the position of the sensor on the picture not the actual physical sensor location. Either way the new sensor position is received and the sensor table is updated, as represented by blocks 636, 638, and 640. Further, the operator can update the sensor information, such as display priority, sensor name, or sensor network id, as represented by blocks 642, 644, and 646. In one example, the sensor information must be updated when a broken sensor is replaced with a new sensor having a different network id.

The operator can now select another sensor and update either the sensor position or sensor information associated with that sensor, as represented by block 648. If an additional sensor is selected the above described process related to blocks 636, 638, 640, 642, 644, and 646 is repeated. Once the updates have been made to the positions of the sensors or the sensor information, the operator must either save the changes to the sensor mapping file or discard the changes, as represented by block 650. If the changes are saved, software 600 queries whether to initiate a testing routine, as represented by blocks 652, 654, and 656. If the changes are discarded the operator is again presented with the option of updating the sensor position or sensor information, as represented by block 632.

As represented by blocks 654, 656, 658, 660, and 662, once the updates have been made to the displayed picture, the operator can either begin the testing routine, block 656, exit the program, block 660, select a new sensor mapping file, blocks 662 and 620, or select an additional picture associated with the current sensor mapping file, block 662, 626, and 628. The operator, in one example would select an additional picture associated with the sensor mapping file to update the sensor placement or sensor information of a sensor not visible in the previous displayed picture. Further, in one example, the software recognizes sensor position changes or sensor information changes in a first picture and updates the corresponding sensor position or sensor information for the additional pictures including the sensor.

Figure 10:
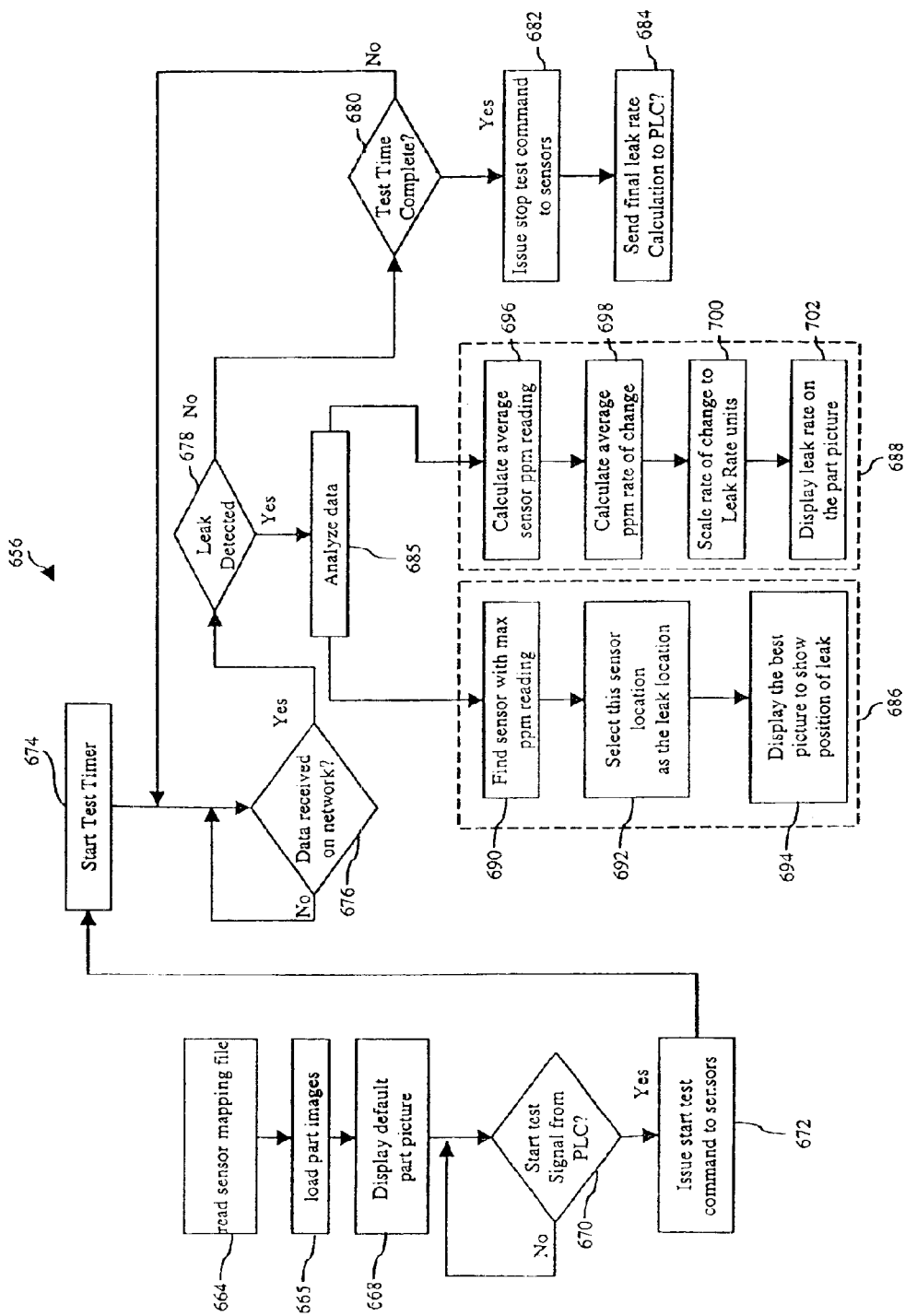
FIG. 10 is a flow chart of the first exemplary embodiment of a testing routine of the operator portion of the leak testing software illustrated in FIG. 9.

Referring to FIG. 10, an example testing routine 656 is shown. As represented by blocks 664 and 665, when a testing routine is initiated the selected sensor mapping file is loaded, block 664, and the associated part images or pictures are loaded, block 665. One of the part images has a parameter value designating that part image as a default part image. The default part image is shown on the display, as represented by block 668. The display of a default image provides a visual cue to the operator that software 600 has loaded the correct sensor mapping file and the corresponding part images.

Software 600 waits for a start test signal from the PLC indicating that the part under test is ready for testing, as represented by block 670. In one example, the signal from the PLC corresponds to the situation wherein part under test 136 has been properly positioned in test region 102, sensors 132 are all in the correct positions, the tracer gas has been properly introduced and the pressure difference between the exterior and interior of the part under test has been established. Once the start test signal is received from PLC 118, a command is issued to all sensors 132 to monitor for the presence of the tracer gas, as represented by block 672, and a test timer is initiated, as represented by block 674. The test timer defines the length of the test for part 136. If a leak is not detected in part 136 during the length of the test timer part 136 is approved. In one example of testing routine 656, testing routine either upon the detection of a leak or expiration of the test timer is reset to begin testing on a second part, wherein the second part is generally identical to part 136. As such, once the operator enters testing routine 656, the operator does not have to cycle through the additional prompts of operator portion 604, such as blocks 620, 624 and 628 before testing the second part.

As represented by block 676, the software monitors network 122 to determine if data is received from a sensor 132 or other component on network 122. If data is received across network 122, the determination is made whether the data corresponds to a detection of the tracer gas, as represented by block 678. In one example, the determination is dependent on whether the amount of tracer gas detected exceeds a threshold value set by a parameter in the sensor mapping file. If the data does not corresponds to the detection of the tracer gas, the test timer is checked to determine if the testing procedure is complete, as represented by block 680. An example instance of data not corresponding to the detection of the tracer gas includes sensor status data, such as sensor 132 is operating properly or that an error has occurred.

Figure 13B:
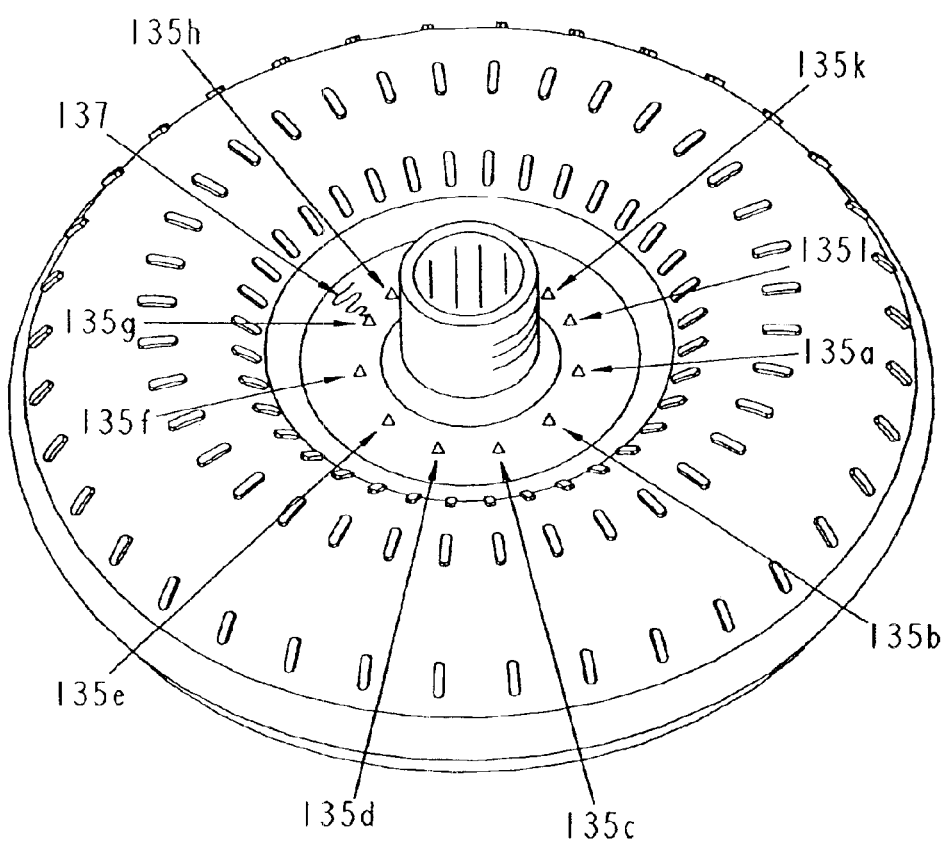
FIG. 13b shows the sensor icons of FIG. 13a and an example of a leak graphic overlaid on a picture of a part under test to provide a visualization cue of a leak emanating from the part under test at the position of the leak graphic.

If the data does correspond to the detection of the tracer gas, then the data and subsequent data is analyzed, as represented by block 685. The data is analyzed to determine the location of the leak, as represented by block 686, a localization routine. In one embodiment, the data is further analyzed to determine the rate of the leak, as represented by block 688, a leak rate routine. Leak rate routine 688 is executed generally simultaneous with localization routine 686. Both localization routine 686 and leak rate routine 688 provide information to generate an indication of a leak in part 136, such as a visualization of the leak on a picture or image of the test part to easily allow the operator to note the location and size of the leak. For example, a leak graphic 137 as shown in FIG. 13B to represent the detection of a leak by sensor 132f. Additional indications of the leak include a signal sent by controller 108 to a remote device, such as a computer in quality control or in the manufacturing area, a visual text message on the HMI unit associated with PLC 118, an audible alarm, or a visual cue such as a flashing light.

Localization routine 686 determines the location of the leak by finding the sensor which is detecting the largest concentration of the tracer gas, as represented by block 690. The location of the leak is correlated to the location of this sensor, as represented by block 692. The picture of part 136 that provides the optimal viewing of the location of the leak is automatically selected and displayed along with an indication of the leak location, as represented by block 694. The picture to display is based on the display preference set for the sensor in the sensor mapping file. In a first example, flashing the corresponding sensor icon or changing the color or other attribute of the corresponding sensor icon is a visual cue of the leak location. In a second example, as shown in FIG. 13B, the leak location is shown by leak graphic 137 representing the emanating of the tracer gas from the leak location. In a further example, the leak graphic of FIG. 13B is an animated graphic such that the graphic simulates gas emanating from the leak location. In yet a further example, the leak graphic flashes to further indicate the location of the leak. Both exemplary sensor icons and leak graphics are shown in FIG. 13B.

In an alternative embodiment, the location of the leak is determined by the sensor which was the first to detect the tracer gas. In a further alternative embodiment, the location of the leak is determined by the sensor which is the first to detect a presence of the tracer gas above a threshold level. In yet a further alternative embodiment, wherein two adjacent sensors both report similar detections of the tracer gas, the location of the leak is determined to be between the location of the two adjacent sensors, such as halfway between the sensors or closer to a first sensor of the adjacent sensors due to a relative weighting of the values reported by each sensor.

It is further contemplated that the part under test might include more than one leak. Multiple leaks may occur in the same potential leak region or in differing potential leak regions. When sensors in differing potential leak regions each report the detection of a leak, the above location routine 686 and the rate routine 688 are conducted for each region. In the instance wherein multiple leaks are in the same potential leak region, the software recognizes multiple leaks by the detection of the tracer gas by two non-adjacent sensors giving rise to a leak condition. For instance, two non-adjacent sensors each record a local maximum of tracer gas concentration or two non-adjacent sensors each record the presence of the tracer gas before the intervening sensors record the presence of the tracer gas.

In the case of multiple leaks it is possible to show multiple images of the part under test on the display at the same time, such as a split screen. The multiple views of the part under test is required because the preferred view of each sensor might be a different image or at least one of the sensors corresponding to a leak is not visible in the preferred image of the other sensor.

Leak rate routine 688 is configured to determine the leak rate of the identified leak. As represented by block 696, for the sensor array detecting a leak the readings from each sensor associated with that sensor array is summed and then averaged. Further, this average sensor reading is monitored over time and an average rate of change in the average sensor reading is calculated, as represented by block 698. In a typical leak testing situation the testing cycle and leak size are such that the rate of change of average sensor readings is generally linear. As such, determining the slope of a line approximating the average sensor readings over time approximates the leak rate.

The rate of change in the average sensor readings is scaled to leak rate units, as represented by block 700. In one example, the scaling is accomplished by comparing the determined slope rate from the block 698 and slope rates for known leaks taking into account the accumulation volume of the fixture containing the sensors, such as fixture 133. The rate of change in the average sensor readings is directly proportional to the leak rate of the leak and inversely proportional to the volume of the accumulation volume. Further, the leak rate is displayed on the part picture or image along with the leak location determined by the localization routine 686. In one example, the leak rate is shown as a numeric value proximate to the leak location. In another example, the leak rate is simulated by the selection of the leak graphic to use to simulate the leak (see FIG. 13B). For example, a graphic showing a large leak emanating from the leak location is used for a high leak rate while a graphic showing a small leak emanating from the leak location is used for a small leak rate.

Figure 11:
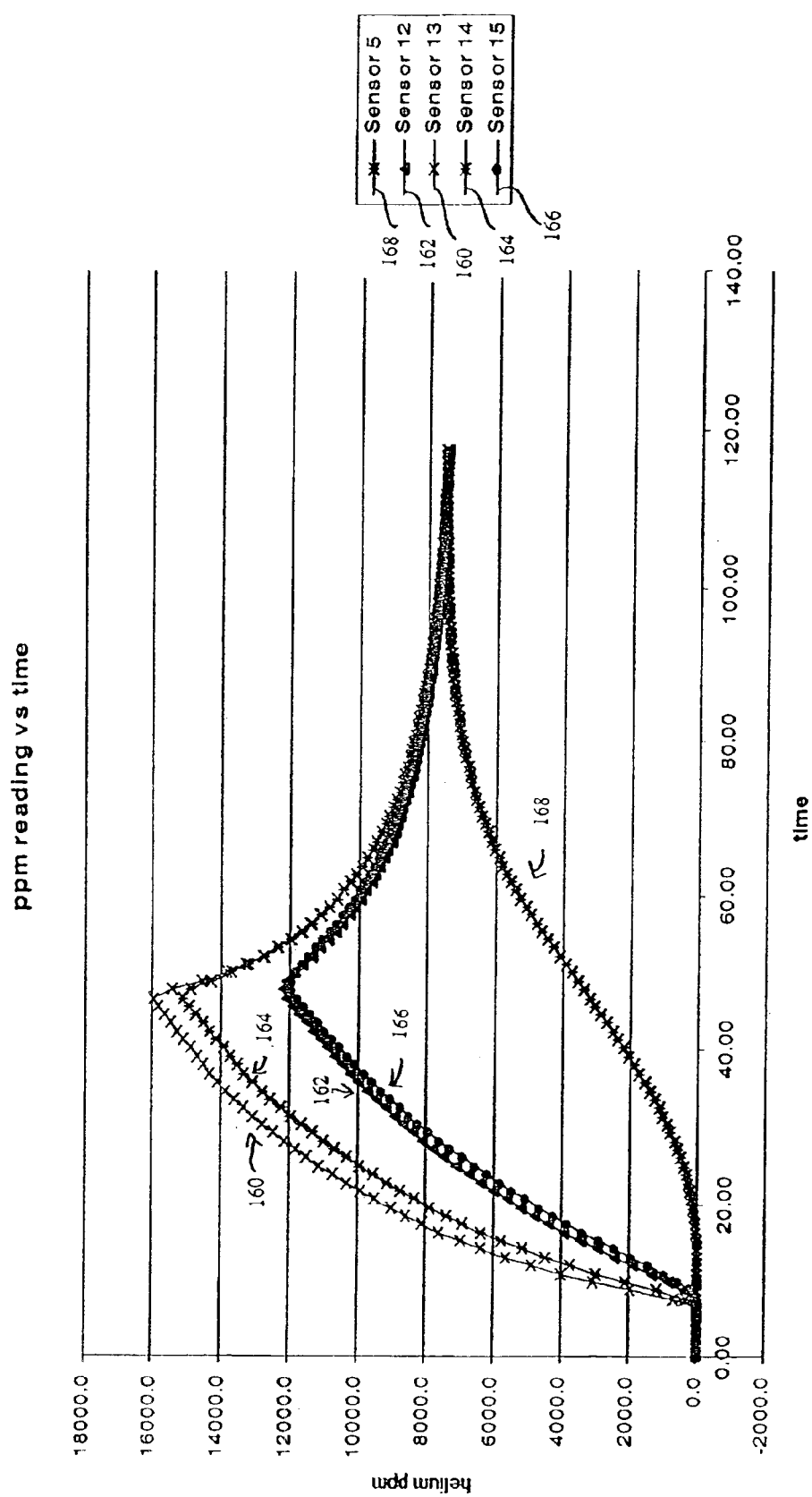
FIG. 11 is experimental sensor output of the leak testing apparatus of the present invention, the experimental data related to a first exemplary leak test showing the output data of five of the sixteen sensors used in the leak test.
Figure 12:
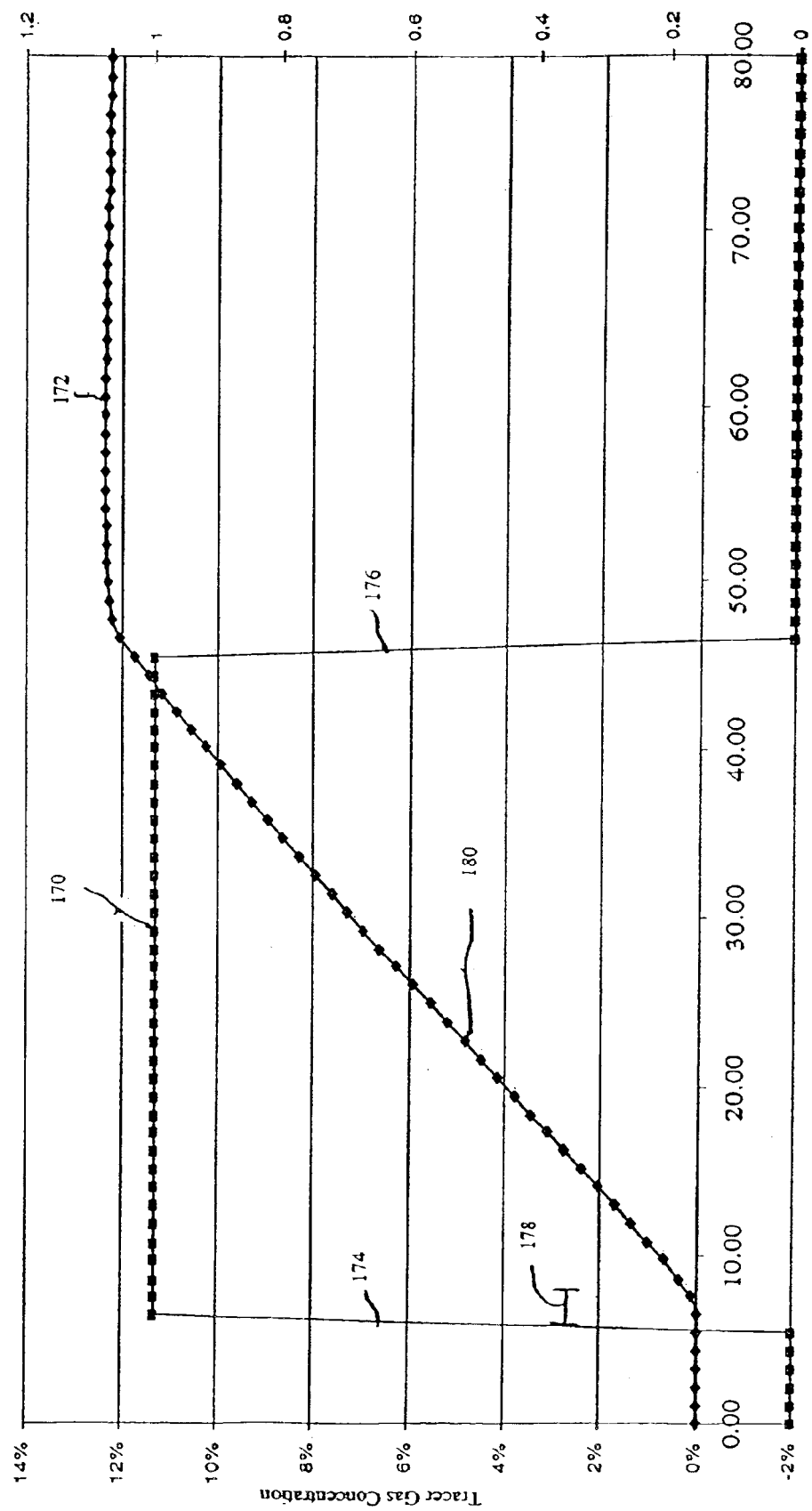
FIG. 12 is sensor output data of the sensors in a leak testing apparatus showing the linear relationship of the average concentrations of tracer gas measured by all of the sensors in a sensor array as a function of time.

Referring to FIGS. 11 and 12, example sensor output corresponding to the leak testing of part 136 with leak testing apparatus 100 is shown. For the example shown in FIGS. 11 and 12, a known leak 144 was introduced into the part in the vicinity of potential leak region 134. Known leak 144 was created by in part 136 by inserting a calibrated leak standard through part 136. Further, known leak 144 was sized to have a known leak rate equal to 0.1 scc/min (standard cubic centimeters per minute). In order to test leak testing software 600, the tracer gas is provided to interior 142 of part 134 through a valve such that the response time of system 100 can be determined.

FIG. 11 provides the individual sensor readings over time for five of the sixteen sensors positioned proximate to the potential leak region. The five selected sensors correspond to the four sensors closest to leak 144 and a sensor distal to leak 144. It should be noted that sixteen sensors exceeds the twelve sensors 132a–l illustrated in FIGS. 3–5. As such, the results shown in FIG. 11 should be able to provide a more accurate location of leak 144 than the results of the twelve sensor arrangement shown in FIGS. 3–5.

Looking at FIG. 11, the sensor denoted as sensor 13 shows the first detection of the tracer gas and also exhibits the highest recorded concentration of the tracer gas as represented by data series 160. The sensors denoted as sensors 12, 14, and 15 are proximate to sensor 13 and denoted by data series 162, 164, and 166, respectively. Each of sensors 12, 14, and 15 detect the presence of the tracer gas slightly after sensor 13 and each of sensors 12, 14, and 15 detect lower concentrations of the tracer gas than sensor 13. As such, the location of leak 144 is proximate to sensor 13. However, it should be noted that the strong response of sensor 14 and the similar responses of sensors 12 and 15 suggests that the leak is positioned roughly halfway between sensors 13 and 14. Further, data series 168 corresponding to the sensor denoted sensor 5 which is distally positioned relative to sensor 13 is included to demonstrate that sensors farther from the location of leak 144 lag in the detection of the tracer gas and the measured concentration of the tracer gas over sensors that are more proximate to leak 144 such as sensors 12, 14, and 15.

Referring to FIG. 12, two data series 170 and 172 are shown. Data series 170 corresponds to the turning on of leak 144, represented by portion 174 of series 170, and the turning off of leak 144, represented by portion 176 of data series 170. Leak 144 is turned on by introducing tracer gas to interior 142 of part 136 through a valve and is turned off by shutting the valve. Data series 172 corresponds to the average value of the concentration of tracer gas for all of the sensors in the sensor array over time. Looking at FIG. 12, the response time of the system is very good. Within approximately three seconds the linear region 180 of data series 172 is developing suggesting that for a leak the size of known leak 144 the system is capable determining the leak rate within approximately three to five seconds. Further, the region 180 of series 172 is very linear, suggesting that the slope of region 180 will provide a good approximation of the leak rate of leak 144.

Returning to FIG. 10, the test timer takes precedence over localization routine 686 and rate routine 688. As such, when the test timer has expired, a stop command is issued to the sensors, as represented by block 682. Further, a final leak rate is calculated and sent to the PLC, as represented by block 684. Alternatively the final leak rate is made available to additional devices on network 122.

Sensor Apparatus for the Detection of a Gas

Figure 14:
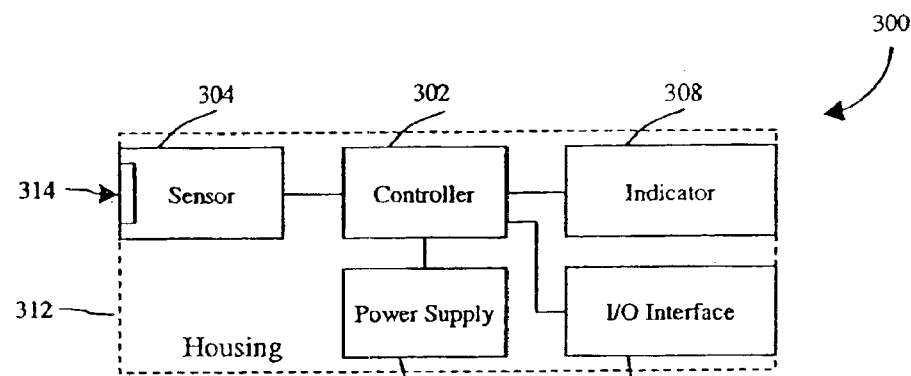
FIG. 14 is a diagrammatic representation of a dual mode sensor apparatus configured to detect the presence of a tracer gas.

Referring to FIG. 14, a sensor apparatus 300 is shown. Sensor apparatus 300 is configured to detect the presence of a gas, such as a tracer gas and to provide an appropriate output to communicate the detection of the presence of the gas. In a first application sensor apparatus is configured to detect the presence of a tracer gas, such as helium or hydrogen, in a leak testing application. In a second application sensor apparatus 300 is configured to detect the presence of a gas, such as helium or hydrogen, and to be incorporated into the design of a component as a safety sensor, example components includes automobiles, trucks, aircraft, boats, and subsystems thereof such as fuel systems, exhaust systems, passenger cabin systems and cargo systems.

Sensor apparatus 300 in one example is capable of detecting concentrations of Helium, a tracer gas, in the range of about 0 ppm (parts per million) to about 5000 ppm and having a resolution of about 25 ppm. In another example sensor apparatus 300 is capable of detecting concentrations of Helium, a tracer gas, in the range of about 0 ppm to about 5000 ppm and having a resolution of about 5 ppm. In yet another example, sensor apparatus 300 is capable of detecting concentrations of Helium exceeding about 5000 ppm.

Sensor apparatus 300 is capable of operating in one of two modes of operation. In a first mode of operation, sensor apparatus 300 is a self-contained sensor apparatus or a self-contained leak testing apparatus and provides an indication to the operator of the detection of the gas, such as the tracer gas, by sensor apparatus 300. In a second mode of operation, sensor apparatus 300 provides a signal to a remote controller, the signal including information related to the detection of the gas such as the tracer gas by sensor apparatus 300. Both modes of operation are described in detail below. In one example of the second mode of operation, sensor apparatus 300 is a networkable sensor that provides a signal to the remote controller over a network.

When sensor apparatus 300 is capable of operating in both modes of operation, although not necessarily both modes at the same time, sensor apparatus 300 is a dual mode sensor apparatus or a dual mode leak detection apparatus. However, it is within the scope of the invention that sensor apparatus 300 is configured to only operate in either the first mode of operation, see generally sensor apparatus 300' in FIG. 15, or the second mode of operation, see generally sensor apparatus 300'' in FIG. 16.

Referring back to FIG. 14, sensor apparatus 300 is a dual mode leak detection apparatus and comprises a controller 302 connected, either directly or through additional components, to a sensor 304, a power supply 306, an indicator 308 and an I/O interface 310. Controller 302, sensor 304, power supply 306, and indicator 308 are enclosed in a housing 312. However, indicator 308 is at least viewable from the exterior of housing 312 and I/O interface 310 is accessible from the exterior of housing 312. Further, a sensing element or transducer 314 of sensor 304 is accessible from the exterior of housing 312 and is positioned generally proximate to the exterior of housing 312. As such, sensor apparatus 300 does not require that the gas to be tested for the presence of the tracer gas be drawn to or past an internal sensing element.

As explained in more detail below, sensor 304 is configured to detect the presence of a gas, such as a tracer gas, and to provide a sensing signal to controller 302, the sensing signal being indicative of the presence or absence of the tracer gas and the amount or magnitude of tracer gas detected. In one example the sensing signal is proportional to the concentration of the detected tracer gas. Power supply 306 is configured to provide power to controller 302, sensor 304, indicator 308, and/or I/O interface 310. Indicator 308 is configured to provide an indication to the operator of sensor apparatus 300 of the detection of the tracer gas and/or the amount of tracer gas detected. I/O interface 310 is configured to provide an output signal to an external device, the output signal being representative of the detection or lack of detection of the tracer gas and/or the amount of tracer gas detected. Further signals are also contemplated, such as an error signal or a sensor status signal. In one embodiment I/O interface 310 is configured to link sensor apparatus 300 to a network.

Controller 302 is configured to receive the sensing signal from sensor 304 and to analyze or make additional determinations based on the sensing signal from sensor 304. Further, controller 302 is configured to provide an indication signal to indicator 308, the indication signal being representative of the detection or lack of detection of the tracer gas and/or the amount of tracer gas detected, or controller 302 is configured to provide an I/O signal to I/O interface 310, the I/O signal being representative of the detection or lack of detection of the tracer gas and/or the amount of tracer gas detected, or controller 302 is configured to provide both an indication signal to indicator 308 and an I/O signal to I/O interface 310.

Figure 15:
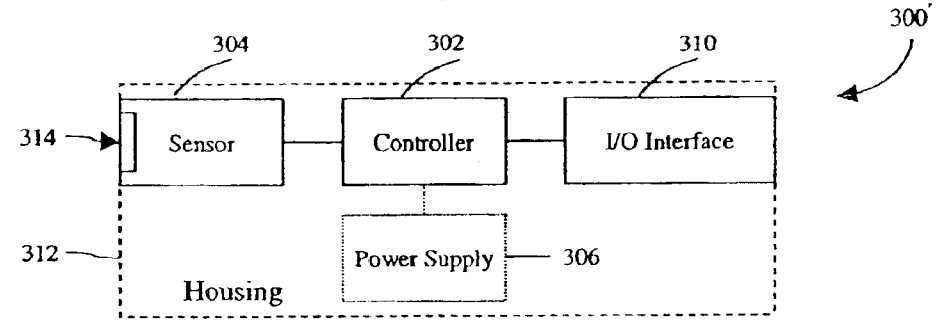
FIG. 15 is a diagrammatic representation of a sensor apparatus configured to detect the presence of a tracer gas and to provide an output signal to a remote device.

Referring to FIG. 15, sensor apparatus 300' is shown. Sensor apparatus 300' is generally similar to sensor apparatus 300 when sensor apparatus 300 is configured to operate in the second mode of operation. As such, like numerals are used for components that are common to both sensor apparatus 300 and sensor apparatus 300'. Sensor apparatus 300' provides a signal to a remote controller (not shown), the signal including information related to the detection of the gas by sensor apparatus 300. In one example, sensor apparatus 300' is configured to be linked to a network. As such, sensor apparatus 300' is generally similar to sensor apparatus 300 expect that an indicator, such as indicator 308 is not needed. In addition since sensor apparatus 300' is connected to a remote controller through I/O interface 310, the power needed by controller 302 and sensor 304 can be provided through I/O interface 310 instead of power supply 306. Alternatively, power supply 306 is included in sensor apparatus 300' in situations wherein a remote power supply is not available, such as a wireless network. Further, the electronics of sensor apparatus 300', although generally similar to the electronics of sensor apparatus 300 may be simpler at least due to the fact that sensor 300' does not need to supply an analog output, does not need to control an indicator, and does not need to control a power supply.

Figure 16:
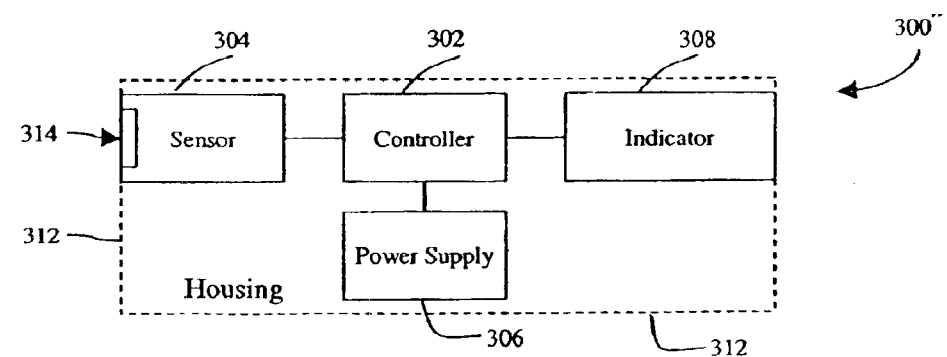
FIG. 16 is a diagrammatic representation of a sensor apparatus configured to be a stand alone leak detector.

Referring to FIG. 16, sensor apparatus 300" is shown. Sensor apparatus 300" is generally similar to sensor apparatus 300 when sensor apparatus 300 is configured to operate in the first mode of operation which corresponds to a self-contained sensor apparatus that provides an indication to the operator of the detection of the tracer gas by sensor apparatus 300. As such, like numerals are used for components that are common to both sensor apparatus 300 and sensor apparatus 300" Sensor apparatus 300" is generally similar to sensor apparatus 300 except that an I/O interface, such as I/O interface 310 is not required. Further, the electronics of sensor apparatus 300", although generally similar to the electronics of sensor apparatus 300 can be simpler at least due to the fact that the I/O interface is not required and the sensor does not need to configure data and information for transmission over a network.

Figure 17:
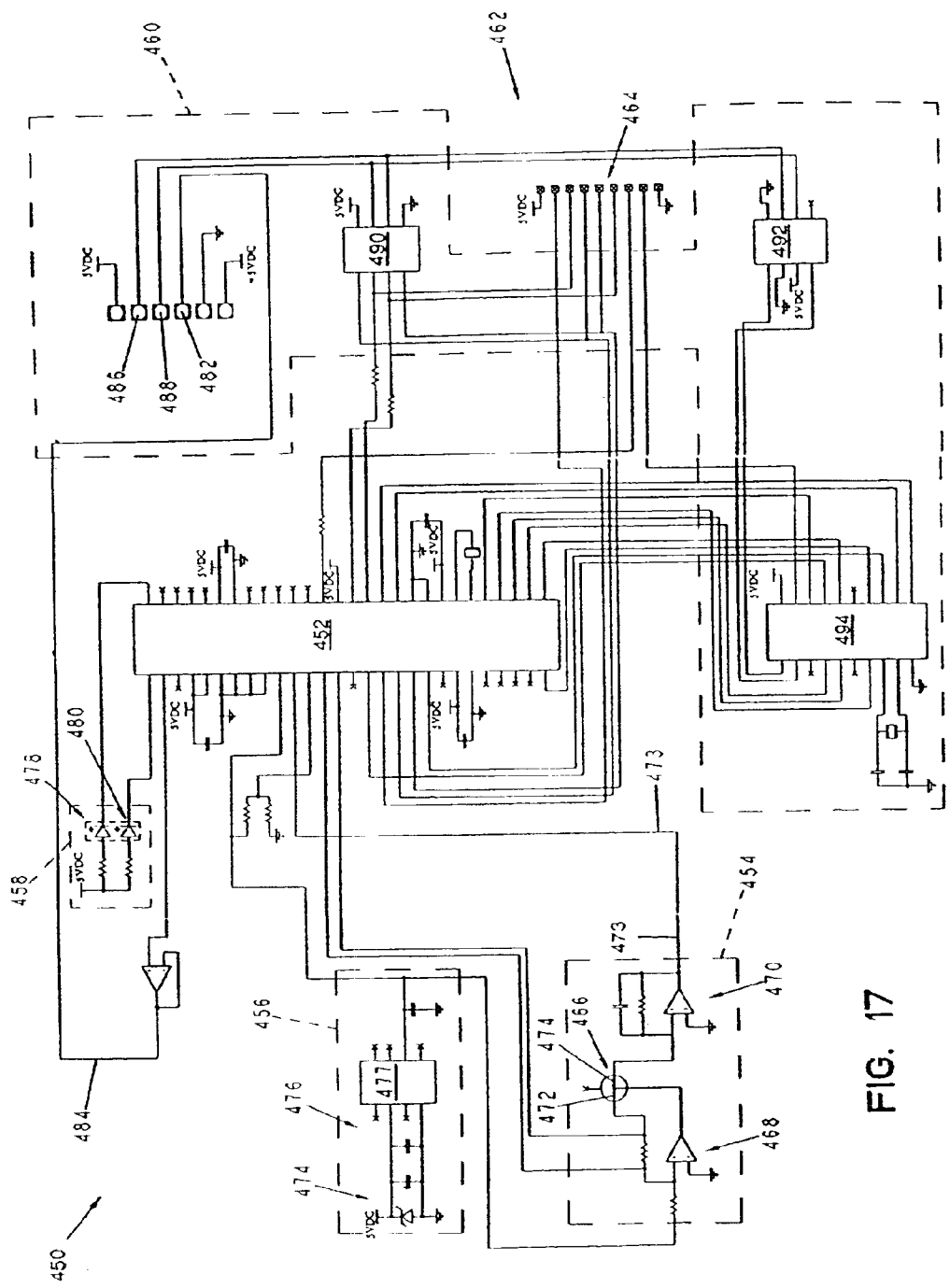
FIG. 17 shows an electronic schematic of a dual mode sensor apparatus of the present invention.

Referring to FIG. 17, one embodiment of a dual mode sensor apparatus 450 is shown. Sensor apparatus 450 is generally similar to sensor apparatus 300 and comprises a controller 452, a sensor 454, a power supply 456, an indicator 458, and an I/O member or interface 460 each being generally similar to controller 302, sensor 304, power supply 306, indicator 308, and I/O member or interface 310 of sensor apparatus 300, respectively. Sensor apparatus 450 further comprises a programming input 462, which includes a series of inputs 464 and is configured to provide programming signals to controller 452 to modify the configuration of controller 452 or a parameter value stored in or accessed by controller 452. In one example, programming unit 452 is used to modify the network ID assigned to sensor apparatus 450 for use with a CAN network.

Sensor 454 of sensor apparatus 450 comprises a thermal conductivity sensor 466 and associated sensor circuitry 468 including an amplifier circuit 470. Thermal conductivity sensor 466 comprises a sensing element or transducer 467 (shown in FIG. 18) such as a membrane (not shown) which is heated above ambient temperature, a measuring resistor or series of resistors 472 which measure the temperature of the membrane and an ambient temperature reference resistor or series of resistors 474 which compensate for ambient temperature changes. As shown in FIG. 18 sensing element or transducer 467 is positioned on the exterior of sensor 466. In the illustrated embodiment, thermal conductivity sensor 466 is Model No. MTCS-2202, available from Microsens SA located at Rue Jaquet-Droz 1, CH-2007 Neuchatel, Switerland. Alternate sensors include other suitable thermal conductivity sensors, acoustic wave transducers, optical feedback transducers, and other suitable sensors capable of detecting the presence of the tracer gas.

Thermal conductivity sensor 466 measures the presence or concentration of a tracer gas by comparing the resistance of measuring resistor 472, which is a measure of the temperature of the membrane, and the resistance of reference resistor 474. Gases that have a lower thermal conductivity than air cause a change in the surface temperature of the sensor membrane and thus a change in the resistance of measuring resistor 472. As such, when the tracer gas is either helium or hydrogen the presence of either helium or hydrogen adjacent the sensor membrane causes a change in the surface temperature of the sensor membrane and therefore a change in the resistance of measuring resistor 472. Further, as the concentration of either helium or hydrogen adjacent the sensor membrane increases the resistance of measuring resistor 472 changes further.

The illustrated sensor circuitry 468 including amplifier 470 are recommended by the manufacturer of thermal conductivity sensor 366, Microsens SA. In alternate embodiments, variations of sensor circuitry are contemplated. The output of amplifier 470 corresponds to the sensing signal of sensor 454 and is provided to controller 452 over connection 473. In one example the sensing signal is proportional to the concentration of the detected tracer gas. The voltage value of the output of amplifier 470 is directly dependent on the resistance of the measuring resistor 472. As such, the detection of either helium or hydrogen by measuring resistor 472 will result in a decrease of the output voltage of amplifier 470.

Power supply 456 comprises a power source 474 represented by the designation "5 VDC" and a voltage regulator 476. It should be noted that the designation "5 VDC" is shown multiple times in FIG. 17 for convenience and that each instance is signifying a connection to power source 474. Power source 474 in one exemplary embodiment is a portable power source, such as a battery. Power source 474, in another exemplary embodiment, is an external power source such as the output of an AC adapter connected to a standard electrical outlet. Further, power source 474, in yet another embodiment, is an external power supply, which provides power to sensor apparatus 450 through I/O interface 460.

Voltage regulator 476 is configured to provide a generally constant voltage source to sensor 454 and controller 452. In the illustrated embodiment, voltage regulator 476 includes a circuit chip 477 Model No. ADR421, which is available from Analog Devices located at One Technology Way, P.O. Box 9106, Norwood, Mass. 02062-9106.

Controller 452, in the illustrated embodiment, includes a MicroConverter®, Model No. AduC834, available from Analog Devices. Controller 452 is a programmable device and includes a program memory (not shown) and a data memory (not shown). In the present invention controller 452 is configured to receive the sensing signal from sensor 454 over connection 473 and to analyze the sensing signal and/or make further determinations based on the sensing signal and the instructions or program stored in controller 452. In one example, controller 452 digitizes the sensing signal from sensor 454 and scales the sensing signal to generate an output signal to provide to I/O interface 460. In one example, the output signal is an analog singal generated by a digital to analog converter (D/A). In another example the output singal is a digital signal. Further, in one example, controller 452 generates an indication signal to provide to indicator 458.

Indicator 458, in the illustrated embodiment comprises a first light emitting diode ("LED") 478 and a second LED 480. LED 478 provides a light visible from the exterior of sensor apparatus 450 having a first color, such as green. The green light of LED 478 is provided in response to receiving a first indication signal from controller 452 corresponding to a power on state of sensor apparatus 450. As such, LED 478 provides a visual cue to the operator of sensor apparatus 450 that sensor apparatus 450 is receiving power and is functional. In an alternative embodiment, the first LED is controlled by the controller to flash during a warm-up period of the sensor apparatus and to provide a steady signal when the sensor apparatus is ready for testing.

LED 480 provides a light visible from the exterior of the housing of sensor apparatus 450 having a second color, such as red. The red light of LED 480 is provided in response to receiving a second indication signal from controller 452 corresponding to the detection of the presence of the tracer gas by the sensor apparatus 450. As such, LED 480 provides a visual cue to the operator of sensor apparatus 450 that the tracer gas has been detected. In a leak testing application LED 480 provides a visual cue to the operator that the part under test has a leak in the vicinity of sensor 454. In another example LED 480 is a bi-color LED, such as Model No. 591-3001-013 available from Dialight Corporation located at 1501 Route 34 South Farmingdale, N.J. 07727. The wavelength emitted by bi-color LED 480 is dependent on the signal provided to LED 480. For instance, the wavelength can be varied from a generally green wavelength to various shades of a generally orange wavelength and up to a generally red wavelength. As such, in one example bi-color LED 480 provides a visual cue to the operator of sensor apparatus 450 of the concentration of detected tracer gas (green for low concentrations up to red for higher concentrations). In another example, bi-color LED 480 emits a green wavelength for low concentrations and a red wavelength for concentrations exceeding a threshold value. In an alternative embodiment, the second LED is controlled by the controller to flash during a testing period of a leak testing application of the sensor apparatus, to provide a steady signal when the presence of the tracer gas is detected by the sensor, and not emit light if the testing period concludes without the detection of the tracer gas.

Referring to FIGS. 19 and 20, an exemplary embodiment of sensor apparatus 450 is shown including a housing 496. Housing 496 is configured to enclose controller 452, sensor 454, power supply 456 (if included), and indictor 458. Further housing 496 is configured to enclose a portion of member 460, such as CAN transceiver 492, CAN controller 494, and RS-485 transceiver 490. However, as shown in FIG. 19, sensing element or transducer 467 of thermal conductivity sensor 466 is accessible from the exterior of housing 496 and is positioned generally proximate to the exterior of housing 496. Further, as shown in FIG. 20, indicator 458 is at least viewable from the exterior of housing 496.

As shown in FIGS. 19 and 20, a first portion 497 of housing 496 is configured to couple housing 496 to another component, such as fixture 133 shown in FIG. 3 in connection to a leak testing application. In the illustrated embodiment first portion 497 is threaded such that first portion 497 may be threaded into a threaded aperture (not shown). A nut 498 is shown threaded onto first portion 497. Nut 498 assists in controlling the degree of engagement between first portion 497 and the threaded aperture (not shown). A second portion 499 of housing 496 configured to be coupled by a tool. In the illustrated embodiment, second portion 499 is faceted such that second portion 499 may be gripped by a wrench to aid in the engagement or disengagement of first portion 497 with the threaded aperture.

Referring back to FIG. 17, I/O interface 460, in the illustrated embodiment, is configured to provide one of three outputs to external devices. First, I/O interface 460 is configured to provide an analog output through connection 482 which is coupled to controller 452 through connection 484. In one exemplary embodiment, controller 452 provides an analog signal scaled between 0 to 2.5 volts which is representative of the sensing signal from sensor 454.

Second, I/O interface 460 is configured to provide a RS-485 network compatible signal through connections 486 and 488. I/O interface 460 includes a suitable transceiver 490 configured to comply with the RS-485 standard to communicate with other devices configured to comply with the RS-485 standard over a network. RS-485 transceiver 490 is controlled by controller 452 through various connections. RS-485 transceiver 490, in the illustrated embodiment, is Model No. ADM485, available from Analog Devices.

Third, I/O interface is configured to provide a CAN network compatible signal through connections 486 and 488 or additional connections. I/O interface includes a suitable CAN transceiver 492 configured to comply with the CAN standard to communicate with other devices configured to comply with the CAN studied over a CAN network and a suitable network controller, such as CAN controller 494, configured to connect controller 452 and CAN transceiver 492. CAN transceiver 492 is controlled by CAN controller 494 and CAN controller 494 is controlled by controller 452 through various connections with controller 452. CAN transceiver 492, in the illustrated embodiment is Model No. MCP2551 and CAN controller 494 is Model No. MCP2510, both available from Microchip Technology, Inc. located at 2355 West Chandler Blvd., Chandler, Ariz. 85224-6199.

The selection of which output type, analog, RS-485, or CAN, to send an output signal over is under the control of controller 452. In a preferred embodiment, controller 452 of sensor apparatus 450 is programmable to have a plug and play type functionality such that controller 452 is capable of recognizing what type of network including the absence of a network is connected to sensor apparatus 450. The operation of the plug and play functionality and additional functions of controller 302 are discussed with reference to FIGS. 21–24 below.

Figure 21:
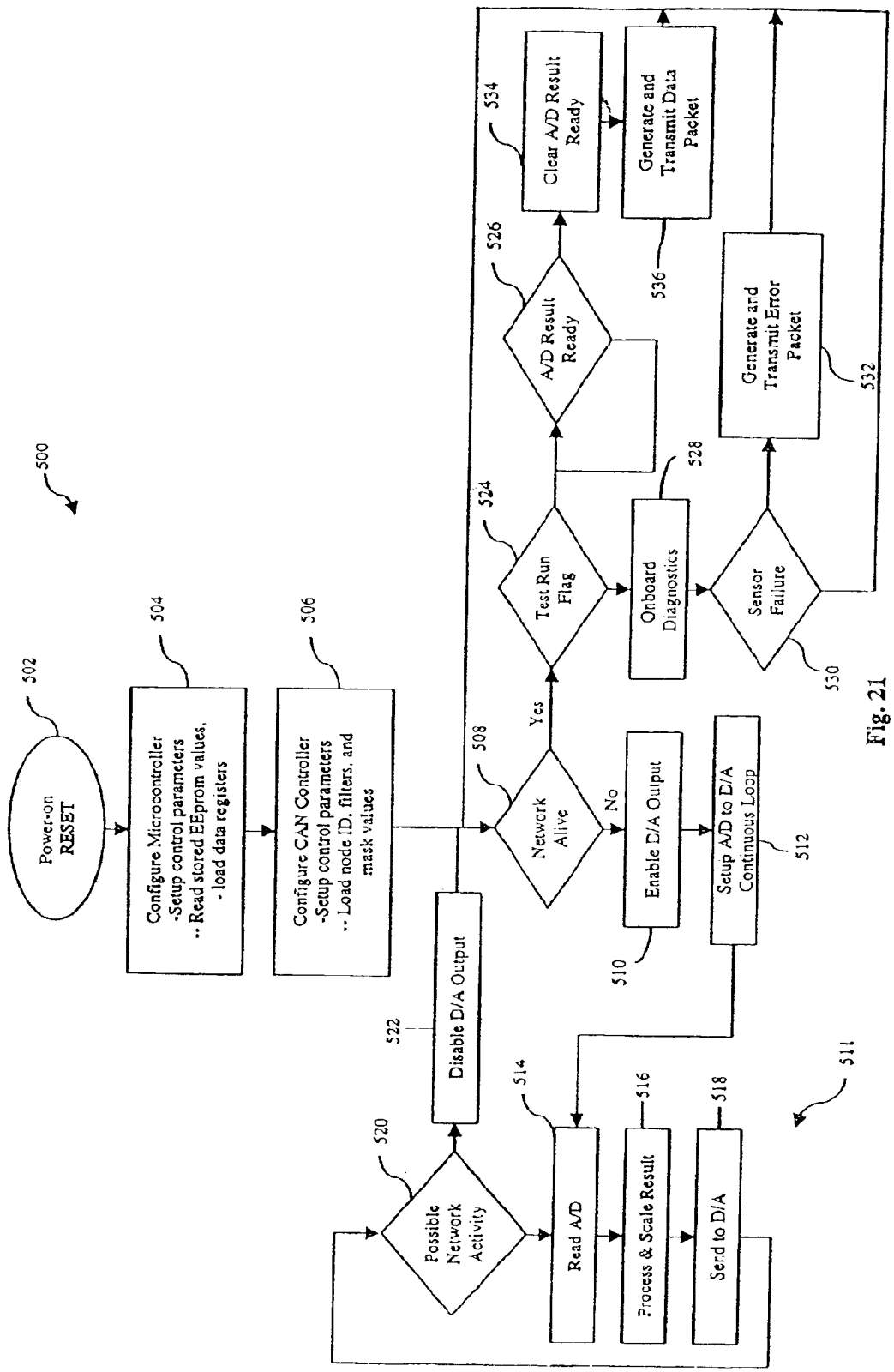
FIG. 21 is a flowchart of a first exemplary embodiment of sensor software for the sensor apparatus.

Turning to FIG. 21, a flowchart of exemplary software 500 configured to provide a plug and play type functionality to controller 302 and to configure controller 302 for a leak testing application is shown. Software 500 includes a power on or reset routine 502 corresponding to functions to be exercised during a reset of sensor apparatus 450 or to delay the operation of further tasks until it is determined that sensor 454 is warmed up and ready to detect the air surrounding sensor apparatus 450. Further, configuration steps 504 and 506 configure the sensor apparatus 450. Configuration step 504 configures controller 452 including loading setup control parameters, such as network address and sensor constants. Configuration step 506 configures CAN controller 494.

Once sensor apparatus 450 is configured, software 500 checks to see if a network is currently connected to sensor apparatus 450, as represented by block 508. If a network is not detected, software 500 enables analog output to be generated by controller 452 through a D/A converter, as represented by block 510. The analog output is then available over connection 482 as explained above. Further, software 500 enables a loop 511 wherein the analog data from sensor 454 is converted to digital data by controller 452 and then reconverted to analog data by controller 452 such that the analog data is accessible through connection 482, as represented by block 512. In one example, the analog data produced by controller 452 is different than the analog data received from sensor 454 due to scaling of the data.

Loop 511 includes the steps of reading the analog data from sensor 454 through an A/D converter, as represented by block 514, process and scale the received data, as represented by block 516, and send the resultant data if any to the D/A converter such that the data is accessible through connection 482, as represented by block 518. In one example, controller 452, processes the data to determine if the data corresponds to the detection of a threshold concentration of the tracer gas and generates appropriate instruction to I/O member 460 and indicator 458. The threshold concentration or value in one example is programmed into sensor controller 452. In another example, the threshold value is communicated to sensor controller 452 from a remote device.

As loop 511 is executing, software 500 is monitoring for possible network activity indicating that a network has been connected to I/O member 460, as represented by block 520. If no network activity is detected, loop 511 continues. However, if network activity is detected the D/A output (the analog output) is discontinued, as represented by block 522 and the network activity is tested to determine if a valid network is connected, as represented by block 508. If the activity is not a valid network, the D/A output is again enabled, block 512, and loop 511 is again commenced.

Assuming a valid network is detected, software 500 checks to see if a test run flag has been set, as represented by block 524. The test run flag is an indication from either controller 452 or a device across the network such as PLC 118 or computer 116 that a leak test application has been initiated. Typically, a leak test application is executed for a specific time frame. As such, sensor apparatus 450 is configured to provide sensing data, such as a sensing signal, during the time frame of the leak test application.

Assuming the run test flag has been set, software 500 checks to see if an A/D result is ready, as represented by block 526. The A/D result corresponding to a digital signal representative of the output of sensor 454. In one example, controller 452 is configured to take a reading from sensor 454 at discrete time intervals, such as about every 100 ms. A value corresponding to the reading, in one example, is stored in a memory accessible by controller 452. As such, software 500 checks to see if a current value has been stored in the memory. If a current value is not stored, software 500 waits for a current value unless an interrupt or other function needs to be performed, such as checking onboard diagnostics, as represented by block 528. An example type of onboard diagnostics is to check for sensor failures, as represented by block 530. If a sensor failure is detected, software 500 generates and transmits an error packet, as represented by block 532, over the network to other devices, such as PLC 118 or computer 116.

If a current value is stored in the memory, software 500 clears the current result from memory, as represented by block 534 and generates and transmits a data packet including the current result from memory, as represented by block 536. The data packet is transmitted over the network to other devices, such as PLC 118 or computer 116.

Figure 22:
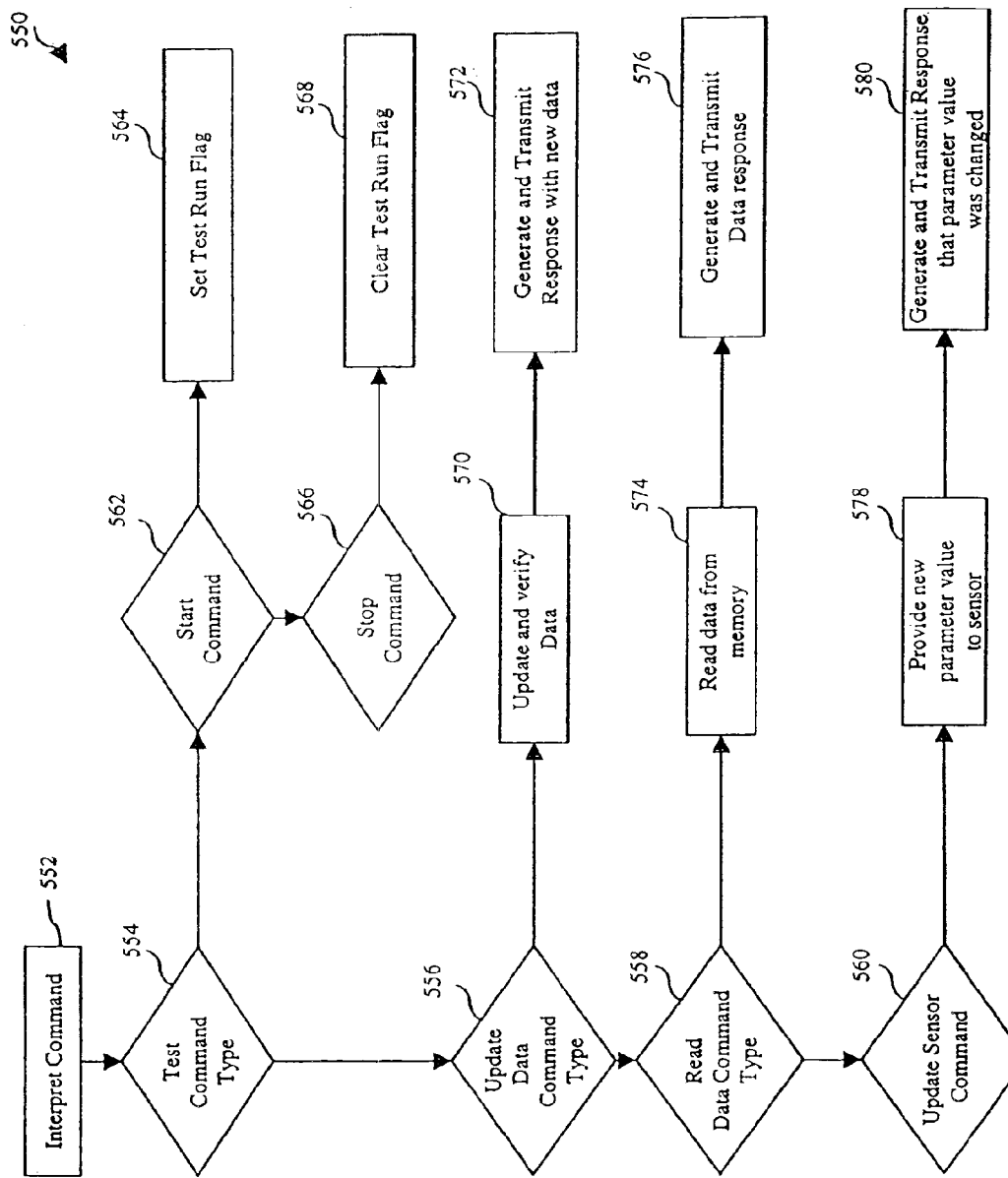
FIG. 22 is a flowchart of a first exemplary interrupt routine of the sensor software of FIG. 21.

Software 500 although discussed in a generally progressive manner is not bound to a progressive execution. In one embodiment, software 500 checks at periodic time intervals for an interrupt routine, or a change in a parameter or flag, or the presence or absence of network activity. A first example interrupt routine 550 is shown in FIG. 22. Interrupt routine 550 corresponds to the reception of a network message across a network, such as a CAN network. The network message includes a command directed at sensor apparatus 450 and configured to either request or command sensor apparatus to perform a function. Software 500 is configured to interpret the command that was sent, as represented by block 552.

Four exemplary command types are shown in FIG. 22. First, a test command type, as represented by block 554, corresponds to commands directed to the initiation or cessation of a testing time period or additional commands related to a testing time period. A first example command, as represented by block 562 corresponds to a test start command. Software 500 in response sets a test run flag to indicate that a test time period has begun, as represented by block 564. A second example command, as represented by block 566 corresponds to a test stop command. Software 500 in response clears a test run flag to indicate that a test time period has ended, as represented by block 568.

Second, an update data command type, as represented by block 556, corresponds to commands requesting that the data from the sensor apparatus be updated or verified. A first example command to update and verify data is represented by block 570. Software 500 in response generates and transmits a response with the requested data, as represented by block 572.

Third, a read data command type, as represented by block 558, corresponds to commands requesting that the data stored in the memory of the sensor apparatus be read and sent. A first example command to read data from a memory is represented by block 574. Software 500 in response generates and transmits a response with the retrieved data, as represented by block 576.

Fourth, an update sensor command type, as represented by block 560, corresponds to commands either requesting the value of a current sensor apparatus parameter or updating a sensor apparatus parameter. A first example command to provide a new parameter value to sensor apparatus 450 is represented by block 578. Software 500 in response generates and transmits a response indicating that the parameter value has been changed, as represented by block 580.

Figure 23:
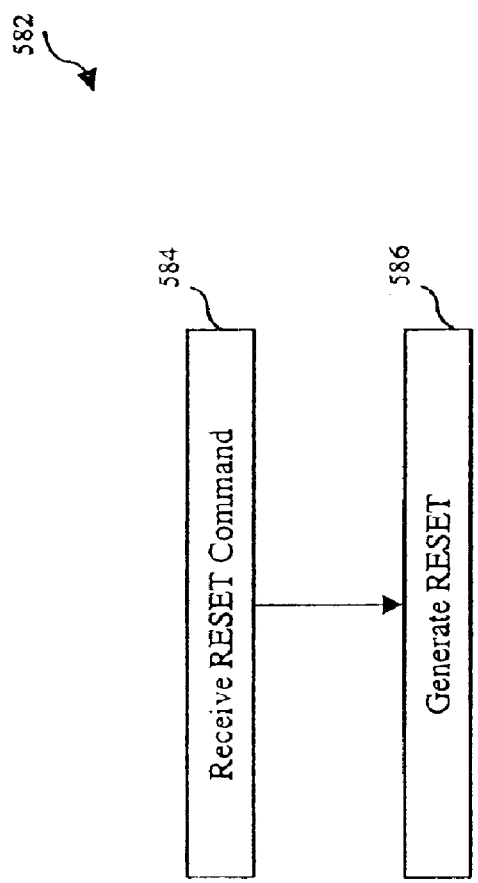
FIG. 23 is a flowchart of a second exemplary interrupt routine of the sensor software of FIG. 21.

A second example interrupt routine 582 is shown in FIG. 23. Interrupt routine 582 corresponds to a watchdog service routine. The watchdog service routine checks to see if a RESET command is received, as represented by block 584 and to generate a RESET of sensor apparatus 450, as represented by block 586. In one example, the RESET command is received across the network. In another example, the RESET command is received due to an operator depressing a RESET button (not shown) located on the exterior of sensor apparatus 450 or otherwise initiating a RESET command. In yet another example, the RESET command is generated by the controller itself, signifying that it has become unstable or is in a locked state.

Figure 24:
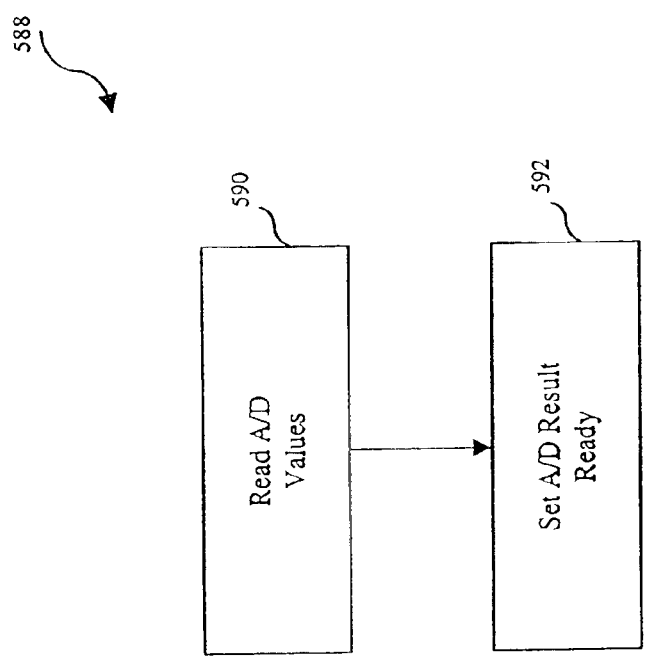
FIG. 24 is a flowchart of a third exemplary interrupt routine of the sensor software of FIG. 21.

A third example interrupt routine 588 is shown in FIG. 24. Interrupt routine 588 corresponds to a A/D Result Ready routine. As explained in connection with FIG. 21, software 500 monitors to see if an A/D result is ready corresponding to a data value from the sensor 454. Interrupt routine 588 is one mechanism by which software 500 determines that a data value corresponding to sensor 454 is available. The interrupt routine 588 includes reading A/D values, as represented by block 590, and to set a A/D result ready flag to let software 500 know that a new data value is ready, as represented by block 592.

In one embodiment of sensor apparatus 450, all or substantially all the electronics of sensor apparatus 450 including sensor controller 452, I/O member 460 including the corresponding electronics for at least one network type, and sensor 454 are all designed to be incorporated into a custom chip (not shown) to reduce the overall size of sensor apparatus 450. In one example the thermal conductivity sensor 466 is coupled to a surface of the custom chip (not shown) containing all or substantially all the electronics. In another example, the thermal conductivity sensor is configured as a component of the custom chip (not shown), such that the sensing element or transducer of the thermal conductivity sensor is positioned on the exterior of the chip or is accessible from the exterior of the chip. By making various connections with the leads of the custom chip a network such as a CAN network or an RS-485 network can be connected to the custom chip. The reduced size of sensor apparatus 450 along with the superior sensing ability of sensor apparatus 450 makes sensor apparatus 450 ideal for incorporation into a component, such as an automobile, as a safety sensor. Sensor apparatus 450 will share information with a controller (not shown) of the component to relay information and data concerning the presence or amount of a gas.

In another embodiment sensor apparatus 450 is configured to operate in a second mode of operation similar to sensor apparatus 300' of FIG. 15 and is designed to be incorporated into a custom chip (not shown) to reduce the overall size of sensor apparatus 450. As such, sensor apparatus 450 does not include an indicator, such as indicator 458. In addition since sensor apparatus 450 will be connected to a remote controller through I/O member 460, the power needed at least by controller 452 and sensor 454 can be provided through I/O interface 460 instead of through power supply 476. In one example the thermal conductivity sensor 466 is coupled to a surface of the custom chip (not shown) containing all or substantially all the electronics. In another example, the thermal conductivity sensor is configured as a component of the custom chip (not shown), such that the sensing element or transducer of the thermal conductivity sensor is positioned on the exterior of the chip or is accessible from the exterior of the chip. By making various connections with the leads of the custom chip a network such as a CAN network or an RS-485 network can be connected to the custom chip. As stated before, the reduced size of sensor apparatus 450 along with the superior sensing ability of sensor apparatus 450 makes sensor apparatus 450 ideal for incorporation into a component, such as an automobile, as a safety sensor. Sensor apparatus 450 will share information with a controller (not shown) of the component to relay information and data concerning the presence or amount of a gas.

Figure 25:
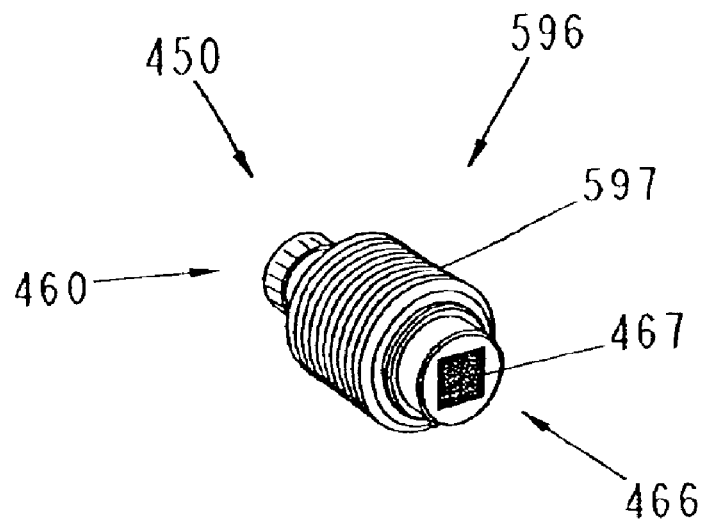
FIG. 25 is a first perspective view of an exterior of a sensor apparatus showing a sensing element accessible from the exterior.
Figure 26:
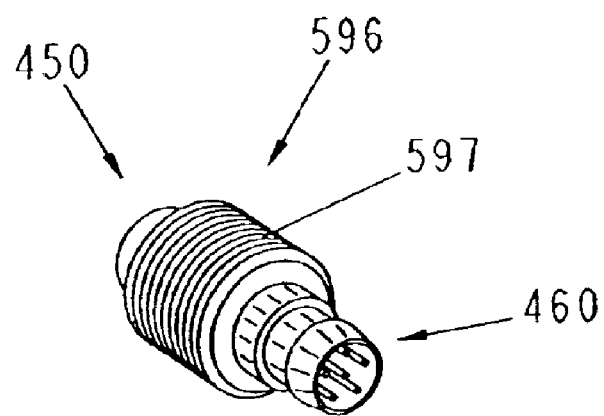
FIG. 26 is a second perspective view of the exterior of the sensor apparatus of FIG. 25 showing an I/O interface.

Referring to FIGS. 25 and 26, an exemplary embodiment of sensor apparatus 450 is shown wherein all or substantially all of the electronics of sensor apparatus 450 are incorporated into a custom chip. Sensor apparatus 450 includes a housing 596, which is configured to enclose the custom chip (not shown) and sensor 454. Further housing 596 is configured to enclose a portion I/O interface 460, such as CAN transceiver 492, CAN controller 494 which may be incorporated into the custom chip (not shown). However, as shown in FIG. 25, sensing element or transducer 467 of thermal conductivity sensor 466 is accessible from the exterior of housing 596 and is positioned generally proximate to the exterior of housing 596. Further, as shown in FIG. 26, I/O interface 460 is accessible from the exterior of housing 596.

Figure 27:
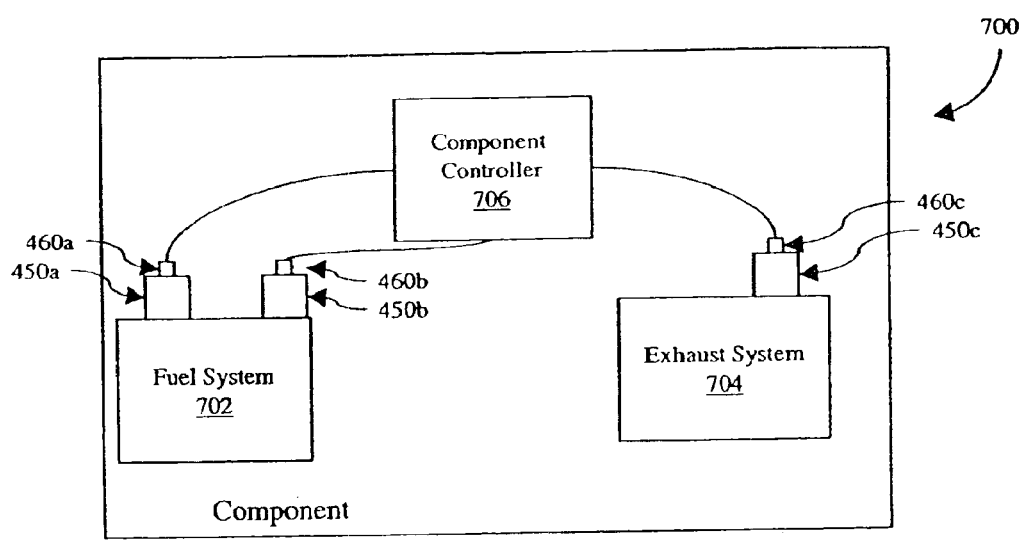
FIG. 27 is a diagrammatic representation of the sensor apparatus of the present invention incorporated as sensors in a component such as an automobile.

As shown in FIGS. 25 and 26, a first portion 597 of housing 596 is configured to couple housing 596 to another component. As shown in FIG. 27, sensor apparatus 450 is positioned in several locations on a component 700, such as an automobile. Sensor apparatus 450*a* and 450*b* are coupled to a fuel system 702 of automobile 700 and sensor apparatus 450*c* is coupled to an exhaust system 704 of automobile 700. Sensor apparatus 450*a*, 450*b*, and 450*c* are connected through I/O interfaces 460*a*, 460*b*, and 460*c* to a component controller 706 of automobile 700.

Although the invention has been described in detail with reference to certain illustrated embodiments, variations and modifications exist within the scope and spirit of the present invention as defined in the following claims.

We claim:

1. A method for sequentially testing multiple instances of a part under test to determine if a first region of the part under test contains a leak, the method comprising the steps of:

positioning a first instance of the part under test in a test region;

introducing a tracer gas such that a first side of the first region of the first instance of the part under test is at a higher pressure than a second side of the first region of the first instance of the part under test;

positioning a plurality of sensors proximate to the second side of the first region of the first instance of the part under test, each of the plurality of sensors configured to detect the presence of a tracer gas emanating from the leak and to provide a sensing signal;

monitoring each of the plurality of sensors for a first period of time to determine if the tracer gas is being detected by any of the plurality of sensors;

providing a leak detection signal in response to at least a first sensor of the plurality of sensors detecting the presence of the tracer gas, the leak detection signal including leak location information representative of the location of the leak in the first region based on the sensing signals received from at least the first sensor and a second sensor of the plurality of sensors;

evacuating the tracer gas from the first side of the first region of the first instance of the part under test;

removing the first instance of the part under test from the test region; and positioning a second instance of the part under test in the test region.

2. The method of claim 1, further comprising the steps of:

introducing a tracer gas such that a first side of the first region of the second instance of the part under test is at a higher pressure than a second side of the first region of the second instance of the part under test;

positioning a plurality of sensors proximate to the second side of the first region of the second instance of the part under test, each of the plurality of sensors configured to detect the presence of a tracer gas emanating from the leak and to provide a sensing signal;

monitoring each of the plurality of sensors for a first period of time to determine if the tracer gas is being detected by any of the plurality of sensors;

providing a leak detection signal in response to at least a first sensor of the plurality of sensors detecting the presence of the tracer gas, the leak detection signal including leak location information representative of the location of the leak in the first region based on the sensing signals received from at least the first sensor and a second sensor of the plurality of sensors;

evacuating the tracer gas from the first side of the first region of the second instance of the part under test;

removing the second instance of the part under test from the test region.

3. The method of claim 1, further comprising the step of providing a first indication of the location of the leak of the first instance of the part under test.

4. The method of claim 3, wherein the first indication includes displaying on a display a first representation of the first instance of the part under test and a sensor icon positioned on the first representation, the sensor icon corresponding to a location of the sensor which is proximate to the location of the leak.

5. The method of claim 3, wherein the first indication includes displaying on a display a first representation of the first instance of the part under test and a leak graphic positioned on the first representation, the position of the leak graphic corresponding to the location of the leak.

6. The method of claim 3, further comprising the step of providing a leak rate signal in response to the at least first sensor of the plurality of sensors detecting the presence of the tracer gas, the leak rate signal including leak rate information representative of the leak rate of the leak.

7. The method of claim 1, wherein the step of providing the leak detection signal includes comparing the sensing signal of the first sensor and the sensing signal of the second sensor, the location of the leak being determined at least in part based on the comparison of the sensing signal of the first sensor and the sensing signal of the second sensor.

8. The method of claim 7, wherein the comparison of the sensing signal of the first sensor and the sensing signal of the second sensor is performed by a controller.

9. The method of claim 8, further comprising the step of providing a first indication of the location of the leak of the first instance of the part under test, the first indication including displaying on a display a first representation of a part under test and a sensor icon positioned on the first representation, the sensor icon corresponding to a location of the sensor which is proximate to the location of the leak.

10. The method of claim 8, further comprising the step of providing a first indication of the location of the leak of the first instance of the part under test, the first indication including displaying on a display a first representation of a part under test and a leak graphic positioned on the first representation, the position of the leak graphic corresponding to the location of the leak.

11. The method of claim 1, wherein the step of positioning the plurality of sensors comprises the steps of coupling at least a portion of the plurality of sensors to a first fixture, the first fixture being moveable between a first position wherein the portion of the plurality of sensors is spaced apart from the first region and a second position wherein the portion of the plurality of sensors are positioned adjacent the first region.

12. The method of claim 11, wherein the first fixture is configured to substantially enclose the first region such that tracer gas emanating from the leak is substantially retained by the first fixture.

13. The method of claim 11, wherein the first fixture and the part under test cooperate to provide a non-evacuated space.

14. The method of claim 1, further comprising the step of providing a leak rate signal in response to the at least first sensor of the plurality of sensors detecting the presence of the tracer gas, the leak rate signal including leak rate information representative of the leak rate of the leak.

15. The method of claim 14, wherein the step of providing the leak rate signal comprises the steps of:
    determining average concentration of tracer gas detected by the plurality of sensors;
    monitoring the change in average concentration of tracer gas detected by the plurality of sensors over a first time period;
    determining the rate of change of the average concentration over time; and
    comparing the rate of change of average concentration to known leak rates.

16. The method of claim 1, further comprising the step of sending the leak detection signal across a network to a remote device.

17. The method of claim 1, further comprising the step of determining if a correlation exists between the location of a leak in a first part under test and the location of a leak in a second part under test.

18. The method of claim 17, further comprising the step of sending the leak detection signal across a network to a remote device.

* * * * *